US012773555B2

(12) United States Patent
Yassur et al.

(10) Patent No.: US 12,773,555 B2
(45) Date of Patent: Oct. 27, 2026

(54) DEVICE FOR STIMULATION OF EYE ACTIVITY

(71) Applicant: BLINKAID LTD, Katzrin (IL)

(72) Inventors: Iftach Yassur, Modiin Maccabim Re'ut (IL); Gal Antman, Ramatt Gan (IL); Alon Tiosano, Kfar Saba (IL); Omer Zarchi, Beit Hashmonai (IL); Raz Karl, Modiin Maccabim Re'ut (IL)

(73) Assignee: BLINKAID LTD, Katzrin (IL)

( * ) Notice: Subject to any disclaimer, the term of this patent is extended or adjusted under 35 U.S.C. 154(b) by 162 days.

(21) Appl. No.: 18/534,872

(22) Filed: Dec. 11, 2023

(65) Prior Publication Data

US 2024/0100335 A1 Mar. 28, 2024

Related U.S. Application Data

(63) Continuation-in-part of application No. PCT/IL2022/050740, filed on Jul. 10, 2022.

(Continued)

(51) Int. Cl.
*A61N 1/36* (2006.01)
*A61N 1/04* (2006.01)

(52) U.S. Cl.
CPC ....... *A61N 1/36046* (2013.01); *A61N 1/0476* (2013.01); *A61N 1/0484* (2013.01);
(Continued)

(58) Field of Classification Search
CPC .............. A61N 1/36046; A61N 1/0476; A61N 1/0484; A61N 1/36034; A61N 1/36014
See application file for complete search history.

(56) References Cited

U.S. PATENT DOCUMENTS 9,625,251 B2 * 4/2017 Heaton ................ A61B 5/1126
10,874,858 B2 * 12/2020 Mowery ........... A61N 1/36034

(Continued)

FOREIGN PATENT DOCUMENTS

WO 2020/132337 A1 6/2020
WO 2021/033139 A1 2/2021

OTHER PUBLICATIONS

PCT International Search Report and Written Opinion for corresponding International Application Serial No. PCT/IL2022/050740, mailed Oct. 4, 2022, pp. 1-10.

*Primary Examiner* — Catherine M Voorhees
(74) *Attorney, Agent, or Firm* — Tarolli, Sundheim, Covell & Tummino LLP

(57) ABSTRACT

A device for stimulating one or more eye functions of individual's eye is presented. The device comprises a stimulator for incorporating in mounting on an appliance attachable to individual's face and comprising respective stimulator arrangement(s) defining an interface region for covering a region of interest on the individual's face in a vicinity of the respective individual's eye. The stimulator arrangement comprises a local controller operating to apply a stimulating effect on one or more nerves in the region of interest to affect predetermined eye function(s), and an array of individually operable stimulating elements each generating a stimulating signal at a respective location in the interface region. The local controller activates a predetermined individual-specific sub-array of the stimulating elements, where locations of the stimulating elements of the sub-array provide a desired spatial pattern of the stimulating effect to be applied while avoiding stimulating effect outside said locations.

22 Claims, 12 Drawing Sheets

Related U.S. Application Data

(60) Provisional application No. 63/220,551, filed on Jul. 11, 2021.

(52) U.S. Cl.
CPC ..... *A61N 1/36003* (2013.01); *A61N 1/36031* (2017.08); *A61N 1/36034* (2017.08)

(56) References Cited

U.S. PATENT DOCUMENTS

| | | | | |
|---|---|---|---|---|
| 11,364,380 | B2 * | 6/2022 | Goodall | A61N 1/36036 |
| 2007/0282012 | A1 * | 12/2007 | Kinoshita | A61B 3/101 514/708 |
| 2018/0161579 | A1 * | 6/2018 | Franke | A61B 5/1127 |
| 2019/0022383 | A1 | 1/2019 | Hadlock et al. | |
| 2020/0360692 | A1 * | 11/2020 | Azar | A61N 1/36046 |
| 2020/0391029 | A1 * | 12/2020 | Mullins | A61N 1/36014 |
| 2021/0138232 | A1 | 5/2021 | Paz et al. | |
| 2022/0047866 | A1 * | 2/2022 | Masko | A61N 1/36046 |

* cited by examiner

FIG. 3A (General Art)

FIG. 3B (General Art)

DEVICE FOR STIMULATION OF EYE ACTIVITY

TECHNOLOGICAL FIELD AND BACKGROUND

The present invention is in the field of medical devices, and relates to a medical device for stimulating eye activity of an individual.

Blinking and tear production are main mechanisms that protect the eye. Blinking serves as a mechanical shield for the cornea, but also disperses the tear film in a thin and even layer, uniformly covering the entire surface of the eye. During a short period lasting between 30-100 milliseconds the innermost circular muscle fibers of the orbicularis muscle constrict (tarsal). Most of the vertical movement is performed by the upper eyelid while the lower eyelid does most of the horizontal movement.

Frequent blinking and tear production are necessary to maintain a healthy eye surface and normal vision. For example, an average person blinks over 15,000 times each day autonomously and unconsciously. Blink rate is controlled by different sensory and psychomotor parts of the brain and is executed by the facial nerve and the orbicularis muscle around the eye. A decrease in the blink rate can impair the quality of vision and even endanger the eye itself.

Blink and dry eye disorders are common in various neurological diseases but are even more common among normal people utilizing their eyes under un-neutral conditions such as extended periods of computer screen time.

People who suffer from dry eye issues, include, for example:

1. Unconscious patients in intensive care units and rehabilitation wards that do not close their eyes spontaneously.
2. Patients with acute or chronic paralysis of the facial nerve on one side (say people with Bell's Palsy) who do not blink because of muscle paralysis. In these patients, optimal blink restoration also involves synchronization of the blink to the healthy eye.
3. Patients with Parkinson's disease with blinking disorder due to a general decrease in motility and facial mimics.
4. The largest group of all, includes people who spend many hours in front of computer screens and cell phones.

GENERAL DESCRIPTION

There is a need in the art for a novel medical device for monitoring, controlling, and affecting such eye activity as blinking and/or tear production.

The present invention provides a novel approach for configuration and operation of such medical device capable of artificially stimulating eye activities/functions. More specifically, the invention provides a stimulator which can be incorporated in a wearable or attachable appliance to be attached to individual's face (i.e., being incorporated within the frame of glasses or a label/pad) or may be autonomous device configured to attachable to a wearable appliance, such as glasses. The stimulator of the present invention is adapted to be controllably operable to apply a stimulating effect on one or more nerves in the facial region of the user, to thereby effect/induce at least one predetermined activity of an eye of the user. Such eye activity includes blinking and/or tears production.

Considering blinking function/activity, the stimulating effect may be associated with neuro-muscular electrostimulation (NMES) of one or more nerves in a selected region in the vicinity of the eye as to cause contraction of the periocular muscle(s) resulting in eye blinking. The device of the present invention is capable of stimulating blinking function causing full blinking effect (via fully closure of the eye).

The technique of the present invention is aimed at providing personalized solution for stimulating the eye activity, in particular blinking function of individual's eyes and/or tears production. The inventors have found that a facial region, which includes nerves that are responsible for the specific eye activity and thus need to be stimulated, has an individual-specific sensitivity map. This results in that application of a stimulating signal/field to some location(s) within said region, while providing desired eye activity, might cause pain or discomfort, and application of said stimulating signal/field to some other location(s) in the same region may be of the same effectivity with respect to the desired eye activity while eliminating or at least significantly minimizing pain and/or discomfort.

Arrangement/distribution of such different-sensitivity locations (i.e. sensitivity map) varies from individual to individual. On the other hand, it is desirable for a medical device to be suitable for use by various individuals. The present invention provides for adjusting the personalized operation of the stimulator, whose configuration is generally suitable for use by any individual. Moreover, the invention provides for adjusting the stimulator operation for selectively implement stimulation sessions inducing different stimulating effects, each performed in the individual-specific mode.

Further, it should be understood that the individual-specific sensitivity map might be different for the facial regions of interests associated with left and right eyes of said individual. The stimulator of the present invention enables its proper operation based on the sensitivity maps in relation to both such regions interest.

According to the personalized approach of the present invention, the stimulator includes one or two stimulating arrangements for stimulating eye function(s) of one or both of individual's eyes. The stimulating arrangement includes an array of individually operable stimulating elements arranged along an interface region corresponding to a region of interest on individual's face. The stimulator further includes a controller which is adapted (preprogrammed) to activate a selected (individual-specific) one or more (sub-array) of the stimulating elements of each stimulating arrangement to apply the predetermined stimulating effect at selected one or more locations of said element(s), while avoiding application of said stimulating effect outside the selected location(s). The selected one or more locations on individual's facial region, and accordingly the selected one or more stimulating elements within the interface region, are defined in accordance with previously obtained (in a calibration stage) predetermined data indicative of facial nerve's sensitivity maps of the individual.

Thus, according to one broad aspect of the invention, it provides a device for stimulating one or more eye functions of at least one of individual's eyes. The device comprises a stimulator which is configured to be incorporated in or mountable on an appliance attachable to individual's face and comprises a respective at least one stimulator arrangement, the stimulator arrangement defining an interface region for covering a region of interest on the individual's face in a vicinity of the respective individual's eyes, said stimulator arrangement being adapted to be controllably operable by a local controller of the stimulator to apply a stimulating effect on one or more nerves in the region of interest to thereby affect at least one predetermined eye function. The stimulator arrangement comprises an array of stimulating elements, each stimulating element being individually operable by said local controller to generate a stimulating signal at a respective location of said stimulating element within said interface region. The local controller is configured and operable to activate a predetermined individual-specific sub-array of the stimulating elements from said array during a stimulation session, wherein locations of the stimulating elements of the sub-array within the interface region enable a desired spatial pattern of the stimulating effect to be applied while avoiding applications of said stimulating effect outside said locations within the interface region.

In some embodiments, the local controller is configured and operable to utilize predetermined data indicative of an individual-specific facial nerve's sensitivity map of the individual, predetermined at a calibration stage performed once for said individual, to define the selected sub-array of the stimulating elements for use in stimulation sessions.

In some embodiments, the individual-specific facial nerve's sensitivity map is stored in a memory of an electronic circuitry of the stimulator. Alternatively or additionally data indicative of the individual-specific facial nerve's sensitivity map is stored in a memory of a personal communication device of the individual being in data communication with the controller of the stimulator.

The stimulating arrangement may be of any type capable of generating stimulating signals of various types, such as electrical signals, electromagnetic radiation, ultrasonic radiation.

In some embodiments, the stimulator arrangement is configured and operable to generate electric stimulating signals. For example, the stimulator arrangement comprises an electrodes arrangement configured and operable to generate the stimulating effect associated with neuro-muscular electrostimulation (NMES) of said one or more nerves.

In some embodiment, the same electrodes arrangement is configured and operable to generate sensing signals indicative of an electrical activity map of the individual's face within the interface region. These may be Electromyography (EMG) signals.

The present disclosure also provides for using the electrical activity map and specific orientation of the stimulator arrangement with respect to the region of interest to provide a highly personalized selection of electrode elements of the stimulator arrangement to be activated and electrical parameters of the electrodes, so that a stimulation results in a pure, painless blink. Such electrical activity map can be obtained by collecting EMG signals and/or electro-oculography (EOG) signals, and/or Electro-encephalography (EEG) signals. To this end, the same electrodes of the stimulator arrangement can be used.

In some embodiments, the stimulator arrangement comprises first and second electrodes, wherein the first electrode is configured to be attached to and extend along said interface region and is formed by said array of first electrode elements, each being individually operable by the controller to form an electrode pair with the second electrode to apply NMES signal to a respective location of the first electrode element within said interface region. The local controller is configured and operable to activate a selected sub-array of said array of the first electrode elements whose locations define a desired spatial pattern of NMES signals to be applied while avoiding applications of NMES signals outside said locations within the interface region, resulting in safety and optimal nerves' stimulation and muscle contraction.

In some embodiments, the local controller is configured and operable to utilize operational data indicative of a predetermined time pattern of activation of the selected sub-array of the stimulating elements.

In some embodiments, the local controller is configured and operable to communicate with a sensing system providing sensing data indicative of the individual's condition (e.g., individual eyes' condition). The sensing system may be integral with the appliance carrying the stimulator. The sensing system may be an imaging system. Alternatively or additionally, the sensing system may be integral with the stimulator arrangement and configured and operable to provide the sensing data indicative of an electrical activity map of the individual's face within the interface region.

The local controller may be configured and operable to communicate with the sensing system and be responsive to sensing data originated in the sensing system and being indicative of the individual eyes' condition, to selectively activate said selected sub-array of the electrode elements.

The local controller may be configured and operable to affect stimulation of the eye activity via the selected sub-array of the stimulating elements upon identifying, from the sensing data, the individual eye's condition corresponding to absence of said eye activity during a predetermined time interval.

The appliance carrying the stimulator may comprise glasses wearable by individual. Such glasses are one of the following types: vision correcting glasses, sunglasses, vision correcting sunglasses, virtual/augmented-reality glasses.

In some embodiments, the first electrode may be integral with a nose pad of the glasses, and the second electrode may be located in temples of the glasses.

In some embodiments, the medical device (stimulator) is configured to be mounted on the glasses.

In some embodiments, the appliance carrying the stimulator is a label.

The invention, in its another broad aspect, provides glasses wearable by an individual, and comprising the above-described medical device of the present invention.

The invention, in its yet further aspect, provides an eye function stimulation system comprising the above-described medical device, and at least one additional stimulator of a different type.

Such additional stimulator may or may not be integral with the appliance carrying the medical device. The additional stimulator may be is configured and operable to be responsive to sensing data indicative of individual eyes' condition and generate a stimulation effect to notify the individual that the eye function is to be initiated to thereby induce voluntary conscious eye function. To this end, the additional stimulator may include a physical assembly adapted to generate the stimulation effect via a physical contact with individual's body (e.g. a predetermined contact application pattern). Alternatively or additionally, the additional stimulator may include a computerized utility installed in individual's personal electronic device and configured and operable to generate, in response to the sensing data, the stimulation effect embedded in displayed data exposed to individual's eyes to thereby induce voluntary conscious eye function. The sensing system may be carried by the individual's personal electronic device to which user's eyes are exposed.

The present disclosure also provides a novel approach for monitoring and optimizing stimulation of various eye activities, e.g., blinking and tear production. This novel approach is based on the structural and functional properties of the eye.

The front of the eye is a unique organ different from other body parts in many ways, perhaps most significantly so, because it is transparent. The cornea is the window through which light penetrates the eye and reaches the vision receptors, thus cannot benefit from the presence of a protecting skin. Instead, and to maintain its' transparency, it is coated by a thin layer of watery substance—the tear film. Due to evaporation, the film breaks after a while. To preserve its integrity and functionality, delicate balance is required between physical and chemical mechanisms: (1) the blinking reflex, repeatedly spreading new layers of tear film over the eye, (2) the tears' volume and highly sophisticated composition, defining the films characteristics such as vapor pressure, and surface tension, and (3) the environmental conditions the eye experiences, challenging the tears film with temperatures, pressure, humidity etc.

There is a need in the art to provide controllable stimulation of the individual's eye activity (e.g., blinking/tear production effect of individual's eye) by considering the individual's specific eye properties and conditions. This is associated with the following:

As mentioned above, the tear film breaks after a while (due to evaporation), and in order to preserve its integrity and functionality, delicate balance is required between physical and chemical mechanisms. The tear film functionality varies between people and is affected by their origin, age, geographic location, health, occupation and more. Given the multiple variables involved it is not uncommon that the above-mentioned sensitive balance is breached, resulting in the film breaking and leading over time to different ocular surface diseases, expressed as discomfort, pain, vision impairment and more. The longer the period the cornea's external surface (epithelium) is exposed to the environment via cracks at the film, the more extensive is the damage, and the larger the damage, the more tears' formation mechanisms are affected and become impaired. It is only when the tear film heals that the vicious cycle breaks, and the eyes' protection mechanism can recover.

Eye doctors can examine the surface of the eye, assess the films' health and attempt to address evident malfunctions. A simple microscope examination allows physicians to determine if one's tear film maintains continuous integrity or fails prior to the following blink. Using a simple timer, they can define quite accurately the time from blink till when the film breaks. Nowadays treatment approaches revolve around potential flaws in the tears formation mechanisms, defining their quantity and quality (composition). Yet many times the faulted mechanisms, singular, or plural, are unclear and the treatment options, mostly limited to tears substitution and anti-inflammatory eye drops, are insufficient or plainly inefficient.

The blinking mechanism spreads a fresh tear film, time and again, regardless of anything else. A mechanical action that has little to do with the film's properties and the environment. Despite the fact that each blink lasts between 30-100 milliseconds only, and that the average person blinks 15,000 times each day autonomously and unconsciously, it is still the simplest mechanism controlling the tear film formation.

The present disclosure thus also provides a novel approach for optimizing the stimulation operation to meet the above requirements. More specifically, the technique of the present disclosure builds on the known abilities to externally stimulate blinks and tears volume and the known techniques to define individual person's tear film qualities and provides a novel stimulation system and method implementing a calibration procedure for calibrating a time pattern (intervals) of various eye activities.

Generally, this aspect of the present disclosure can be implemented with any known suitable stimulator device, typically of the type including electrode(s) operable to implement such stimulating effect as NeuroMuscular Electrostimulation (NMES) of the facial nerve circuitry to contract the Periocular muscles (eyelid closure muscles). The stimulator unit (i.e., its local controller) is pre-programmed with the individual's specifically chosen (prescribed) time pattern of stimulation signals determined during the calibration procedure of the present disclosure.

Preferably, the stimulation optimization technique of the present disclosure can utilize the above-described device for stimulating one or more eye functions of individual's eye, namely the device including a stimulator with multiple individually operable electrode elements/segments, enabling to provide a desired spatial pattern of the stimulating effect to be applied while avoiding applications of the stimulating effect outside locations within the interface region.

Thus, according to a further broad aspect of the invention there is provided a system to controllably stimulate at least one eye activity utilizing at least one stimulator device configured to stimulate the at least one eye activity of a patient, the system including a controller configured and operable to implement a calibration procedure for calibrating a time pattern of the at least one eye activity, the time pattern being adjusted specifically to patient's parameters obtained during said calibration procedure.

The controller is a computerized device/circuitry which includes an input, an output, a memory and a signal/data processor (processing circuitry), wherein the processor is configured and operable to provide patient's specific calibration function to be used for the at least one stimulator device, the calibration function being configured to perform a patient specific calibrated time pattern to activate the at least one stimulator device.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 3A to 3C exemplify the configuration of the functional parts of the device of the present invention with respect to a nerve circuitry in the facial region of an individual;

DETAILED DESCRIPTION OF EMBODIMENTS

Figure 1:
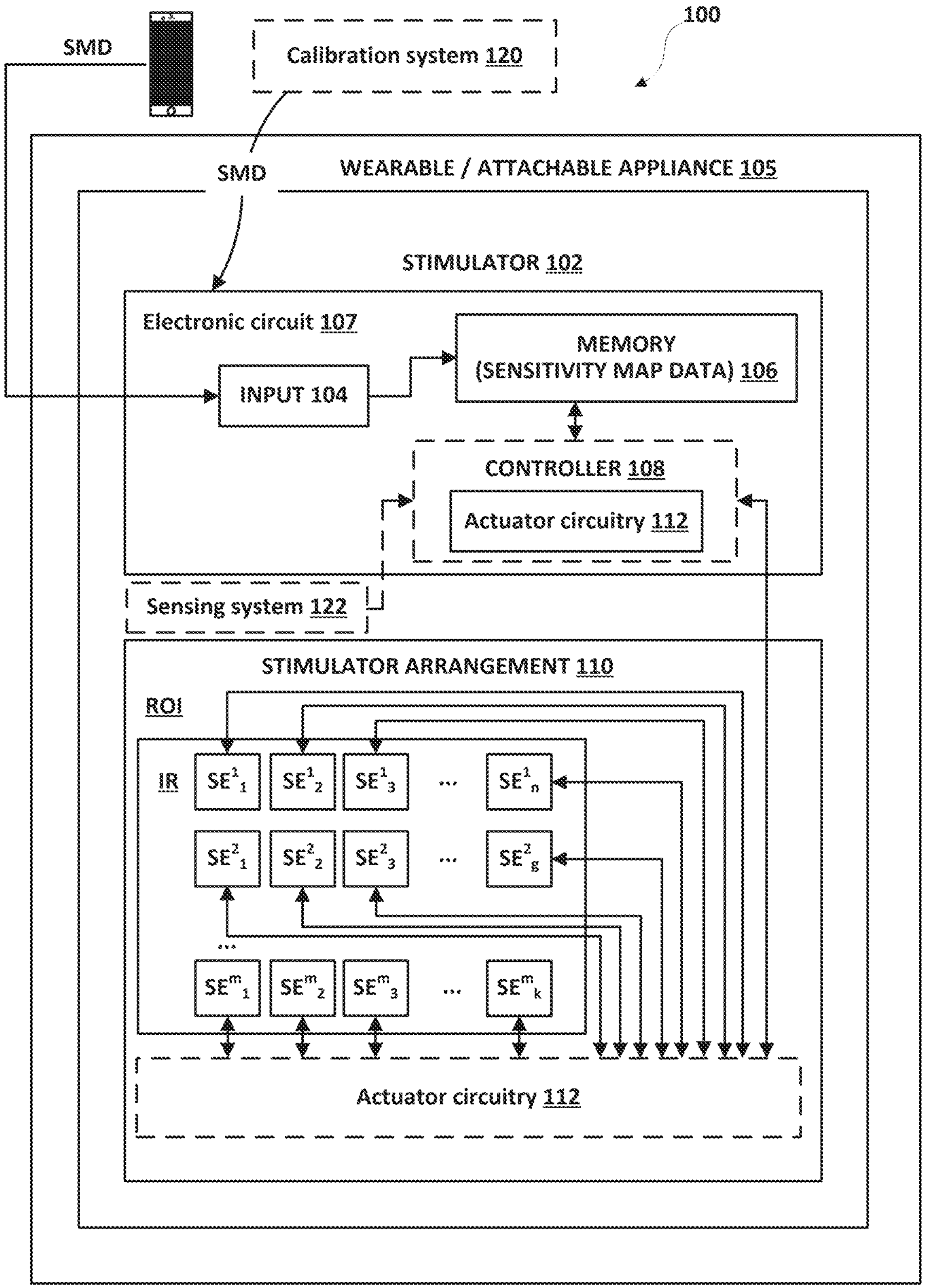
FIG. 1 is a block diagram exemplifying an eye function stimulation device of the present invention.

Reference is made to FIG. 1 illustrating, by way of a block diagram, a medical device 100 of the present invention configured and operable to artificially stimulate one or more eye function/activities of at least one eye of an individual, in particular blinking and/or tears production activities.

The device 100 includes a stimulator 102 which is configured to be incorporated in or mountable on an appliance 105 of the type attachable to/engageable with a region of interest ROI on the individual's face. The region of interest is a region aligned with a nerve circuitry responsible for the desired eye function(s), as will be described more specifically further below.

It should be understood that, in most cases, the same eye activity is to be induced at both eyes of the individual, while it may be the case that only one eye suffers from a specific disorder which is to be treated, or both eyes suffer from the same disorder but at different extents. Thus, generally, the stimulator of the present invention can be configured for one eye treatment only. For example, the appliance 105 may be a label whose side defining the interface region can be glued along the facial region of interest in vicinity of the individual's eye.

However, since the medical device of the present invention is, on the one hand, configured to be used by any individual, while on the other hand is configured to perform personalized (individual-specific) stimulation of the eye function(s), the stimulator may be configured to be integrated in or mountable on the appliance intended to both eyes of the individual. Such appliance carrying the stimulator may be a part of any standard glasses wearable by individual. In this connection, it should be understood that standard glasses/spectacles that can serve the appliance for integration therein or mounting thereon the stimulator (medical device) of the present invention, may be typical vision correcting glasses, or regular or vision correcting sunglasses, or virtual/augmented-reality glasses.

As will be exemplified further below, the stimulator may be incorporated in the nose pads of glasses (or generally in one of the nose pads) which typically contacts with the individual's face; or in some embodiments, some of the functional elements of the stimulator are located in the nose pad(s) of glasses, while some other functional elements of the stimulator are integral with temple(s) of said glasses.

The stimulator 102 includes at least one stimulator arrangement 110 associated with a respective at least one eye of the individual for stimulating eye function(s) of said eye. For simplicity, the figure illustrates only one stimulator arrangement, but it should be understood that when stimulating eye function(s) of both eyes is considered (which is the most practical case), two such stimulator arrangements 110 are provided in association with two respective, substantially symmetric, regions of interest on the individual's face.

Also, the stimulator 102 includes a controller 108 which operates the stimulator arrangement to apply the desired stimulating effect on one or more of the relevant nerves in the facial region of interest, and by this effect at least one predetermined activity of the individual's eye (blinking and/or tears production). According to the invention, the stimulator arrangement 110 includes an array (matrix) of multiple stimulating elements, generally at SE, arranged in a spaced-apart relationship along an interface region IR which is configured to substantially match the region of interest ROI.

As shown in the specific not-limiting example of FIG. 1, the stimulating elements are arranged in a spaced-apart relationship in multiple rows (number M such rows), which include respective pluralities of spaced-apart stimulating elements (of the same or different numbers). It should be understood that, generally, the number and arrangement of the multiple stimulating elements SE depends inter alia on the geometry (dimensions and shape) of the interface region IR of the appliance, which in turn depends on that of the region of interest ROI.

Each stimulating element SE interfaces with (contacts) a respective location within the facial region of interest ROI covered by the stimulator arrangement 110 and is thus aligned with a corresponding location of the nerve circuitry. Each stimulating element SE has its respective identification parameter/index and its location within the interface region IR. Each stimulating element SE is individually operable by the controller 108, via an actuator circuitry 112, to generate the stimulating effect at the respective location of the region of interest.

The actuator circuitry 112 may be part of the stimulator arrangement, or may be part of the controller 108, or the hardware/software utilities of the actuator circuitry may be distributed between the stimulator arrangement and the controller. Considering a pair of stimulator arrangements in association with the individual's eyes, the same controller 108 can be used to properly apply personalized (individual-specific and possibly also eye-specific) operation of each of the stimulator arrangements.

The controller 108 can thus activate a selected one or more of the stimulating elements to be involved in the stimulation session. In the description below such selected one or more stimulating elements are referred to as a sub-array of the stimulator arrangement 110. Generally, however, it might be the case that activating a single stimulating element is sufficient to achieve the desired stimulating effect of the eye.

According to the invention, the selected stimulating elements (selected sub-array) are elements located at selected locations of the interface region IR and thus interfacing/aligned with corresponding selected locations of the region of interest ROI, such that they provide a desired spatial pattern (i.e. fine tuning) of the stimulating effect only at the selected locations, while avoiding application of said stimulating effect outside these locations within the region of interest. To this end, the controller 108 operates to activate the selected stimulating elements in accordance with data indicative of an individual-specific (individual characteristic), and possibly also eye-specific, facial nerve's sensitivity map which is previously created and stored during a calibration stage performed by a calibration system 120.

Sensitivity map data SMD may be entered into an electronic circuit 107 of the stimulator via input utility 104 and stored in a memory 106 of the electronic circuit 107. Alternatively, or additionally, the sensitivity map data SMD may be stored in a memory of individual's personal communication device such as his/her smartphone (as shown in the figure). As will be described further below, the individual's personal communication device may be configured (i.e. installed with a dedicated software application) to perform the calibration stage to create the sensitivity map data for each eye of the individual. It should be noted that, generally, the sensitivity map indicative of the selected sub-array of the stimulating elements may be different for left and right eyes of the same individual. This is properly inspected and defined at the calibration stage.

Thus, the sensitivity map data SMD is obtained by the calibration system 120 during the calibration stage which can be performed once to generate the sensitivity map data for each eye and this data is properly stored in the memory 106 of the medical device 100 or in the external device (e.g. smartphone) which operates the medical device 100. The stage of creation of the sensitivity map data will be described more specifically further below. This sensitivity map data SMD is indicative of the selected spatial pattern (sub-array) of the stimulating elements whose locations are aligned with locations within the nerve circuitry which, when activated induce the stimulating effect while with minimal pain/discomfort for the specific individual. The sensitivity map data SMD may also include data indicative of operational parameters of the selected stimulating elements in said sub-array.

The application of the stimulating effect via activation of the selected group/sub-array of stimulating elements may be performed in accordance with a predefined time pattern of activating and operating the selected stimulating elements, previously defined and stored as part of reference/calibration data to be used by the controller. Alternatively or additionally, activation of the selected group/sub-array of stimulating elements may be performed per demand based on analysis of sensing data. Hence, as exemplified in the figure, in some embodiments, the medical device 100 may also be associated with a sensing system 122, which may or may not be part of the appliance 105. The sensing system 122 is adapted to monitor the individual eyes' condition and generate corresponding sensing data to enable, upon identifying that some critical time has passed without blinking and/or tears production, generation of a control signal to activate the stimulator operation.

Typically, although not specifically shown in the figure, such sensing system 122 includes: an optical unit either configured as a camera which produces image data or a light source and an optical detector to detects light reflection of illumination from the eye. Suitable analyzer (software utility) is thus also provided (being a part of the sensing system 122 or of the controller 108, or distributed software implemented by the sensing system and the controller) which analyzes the image data or the detected reflection data to determine duration of the open eye and/or dry condition of the individual's eyes.

It should be noted that the principles of the present invention can be used with the stimulating arrangement of any known suitable type, i.e. generating stimulating signals of any type, such as electrical signals, electromagnetic radiation, ultrasonic radiation. More specifically, the present invention is useful for stimulating eye activities via electrical stimulation and is therefore described below with respect to this specific application, where the stimulating elements are electrode elements. However, it should be understood that the invention is not limited to this specific implementation.

Thus, in some embodiments, the stimulator arrangement 110 is configured as an electrodes' arrangement, including the matrix of first electrodes (e.g. anodes) operable as stimulating elements, each being in electrical connection with a second electrode (cathode) to form cathode-anode pair. The second electrode may be common for all the first electrodes, in which case the activation of the selected pairs is implemented via the selected first electrodes.

Figure 2:
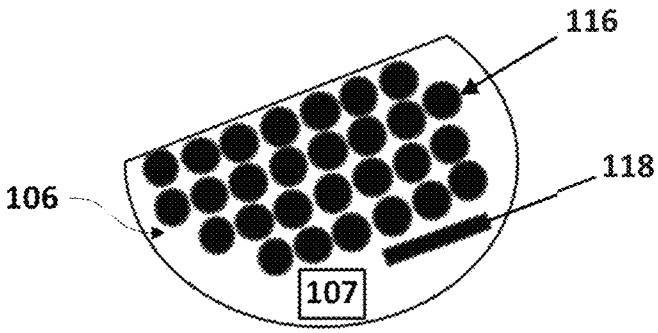
FIG. 2 schematically illustrates an exemplary stimulator of the present invention incorporated in a label.

FIG. 2 schematically illustrates an appliance (e.g. label) 105 incorporating: the stimulator arrangement 110 including the array of first electrodes, generally at 116, all connected to the common second element 118; and the electronic circuit 107 (chip) configured generally similar to that described above with reference to FIG. 1. As indicated above, and will be exemplified further below, the electronic circuit, as well as the second electrode, may be located in a different part of the device while being properly connected or connectable to the first electrodes.

Considering stimulation of such eye functions as blinking and/or tears production, the stimulator 102 may be configured to implement such stimulating effect as NeuroMuscular Electrostimulation (NMES) of the facial nerve circuitry to contract the Periocular muscles (eyelid closure muscles). To this end, the stimulator is operable to apply modulated electrical pulsed signals, via selected locations of the interface region matching corresponding locations of the region of interest.

Figure 3C:
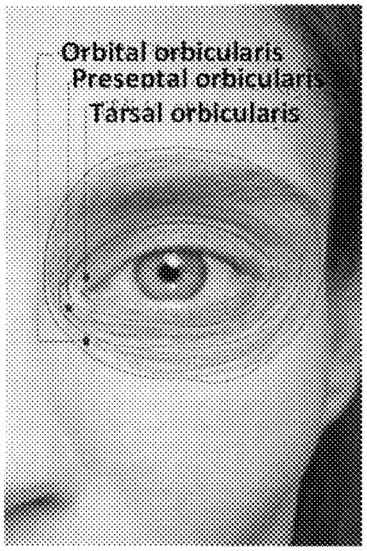
Figure 3C:
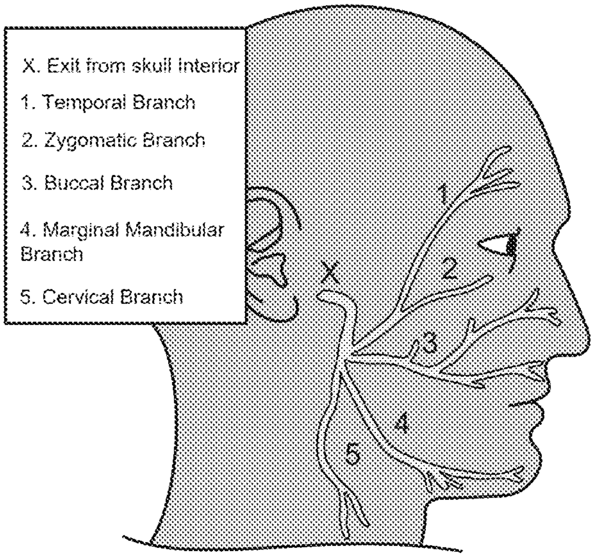
Figure 3C:
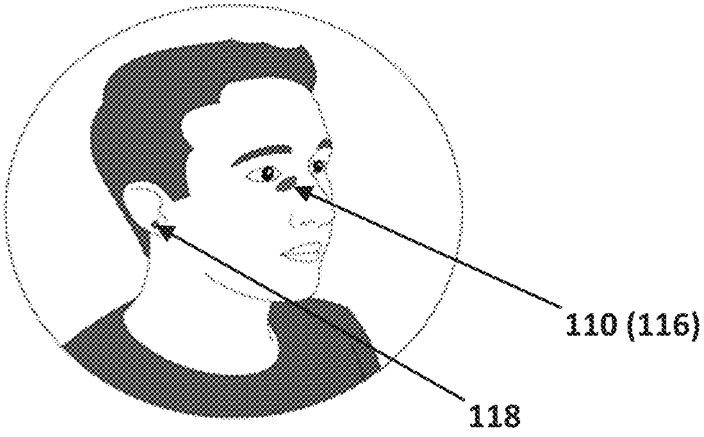

In this connection, reference is made to FIGS. 3A-3C. The present invention pertains to positioning the interface region for transcutaneous electrical stimulation enabling a painless and effective contraction of the orbicularis oculi muscle, as shown in FIG. 3A. The appliance is configured to be positioned such that the interface region of the stimulator is aligned with and allows stimulation of the region of interest which mainly includes the terminal nerve fibers of the buccal (Deep and Superficial) branch of the facial nerve circuitry and possibly also intermingling fibers from the zygomatic or temporal branches (FIG. 3B).

FIG. 3C schematically illustrates an exemplary relative accommodation of the arrangement of first electrodes (anodes—stimulating elements) 116 defining the interface region of the stimulator and the second associated electrode (cathode) 118. It should be noted that the stimulator is preferably configured to enable orientation of the interface region IR of the stimulator medially to an imaginary line crossing the center of the pupil perpendicularly to the pupil plane. This is contrary to the conventional approach in the stimulation devices of the kind specified (i.e. blink stimulators), according to which a stimulator (a continuous elongated electrode) is applied to the facial region such that it is oriented laterally to the perpendicular line crossing the pupil, which results in the stimulation of more proximal branches of the temporal and zygomatic branches, rather than buccal branches.

As for the second electrode (cathode) 118, it may be positioned behind the ear as exemplified in the figure. It should, however, be understood that the second electrode can be placed almost anywhere on the body, including the fingertips. The ear was chosen because it works well with the configuration of glasses.

The operational parameters of the stimulation arrangement may be similar to those used in any known suitable device of the kind specified. However, according to the invention, the stimulation arrangement is configured as described above including an array/matrix of individually operable stimulating elements, enabling to apply the relevant operational parameters to the individual-specific (and possibly also eye-specific) sub-array of the stimulating elements selected in accordance with the individual's sensitivity map.

Considering specific not limiting example of the stimulation arrangement configured to generate electric signals to effect Electrostimulation (NMES) of the facial nerve circuitry to contract the Periocular muscles (eyelid closure muscles), the selected electrode elements can be operated/activated by the following operational parameters/conditions: pulse train (about 20 records) of biphasic square wave pulses (at 250 Hz with 50% peak percentage from the duty cycle); and stimulation waveform parameters including: voltage of about 20-30 volts (this parameters typically varies from individual to individual), electric current in a range of 4-20 mA. Typically, using electrode gel can improve the conductivity and reduce the required voltage by about 30%. The inventors have found that increasing the peak time from the cycle provides a similar effect to increasing the tension; increasing the number of peaks from 20 to 50, while having no significant effect on closing the eye, affects the pain level (a little more painful).

As described, the stimulator itself can be integrated in a label that can be glued to the face region which is engageable by a respective portion of standard glasses. The glasses can thus assist in keeping the label in place and adhering the interface region to the facial region of interest.

It is a practical and simple solution to implement the stimulator of the present invention, e.g. aimed at controlling and stimulating blinking and/or tears production, by integrating the stimulator in or mounting the stimulator on standard glasses, and in particular in/on the suitable components of glasses, for example, the nose pads and possibly also temples. Integrating or mounting the stimulator or at least the part thereof defining the interface region, i.e. the arrangement/matrix of the stimulating elements, within or on the glasses, and in particular in nose pads of the glasses, provides that the electrodes may be properly adhered to the skin through pressure exerted by the structure of the glasses themselves and their own weight. Also, this allows easy removal and replacement of the stimulator arrangement or parts thereof. It should be understood, and also indicated above, that standard glasses/spectacles that can serve the appliance for integration therein or mounting thereon the stimulator (medical device) of the present invention, may be typical vision correcting glasses, or regular or vision correcting sunglasses, or virtual/augmented-reality glasses.

Figure 4A:
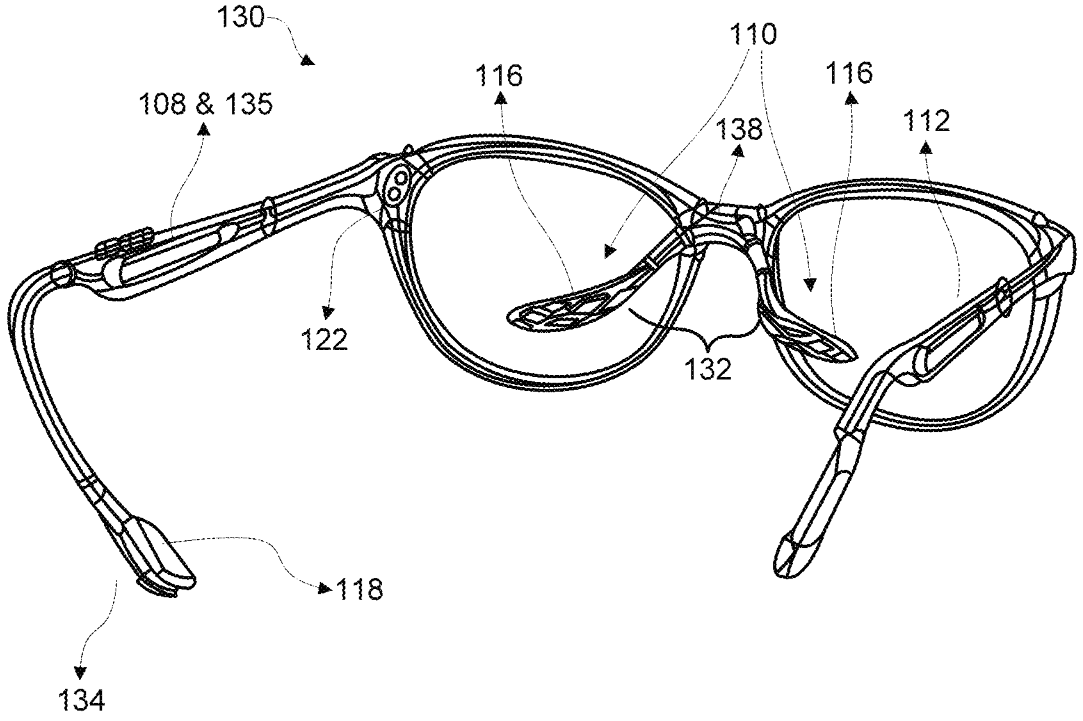
FIGS. 4A to 4F exemplify the device of the present invention configured for integration within or mounting on individual's glasses.

The above is exemplified in FIGS. 4A-4F. FIG. 4A schematically illustrates standard glasses 130 configured as appliance carrying the stimulator 105 of the invention configured to be operable in accordance with individual-specific sensitivity map data for each of individual's eyes. As mentioned above, generally, the sensitivity map data indicative of the selected sub-array of the stimulating elements may be different for left and right eyes of the same individual. This is properly inspected and defined at the calibration stage, which will be described further below.

In this example, the stimulator 105 includes two stimulator arrangements 110 relating to the left and right eyes of the individual. Also, in the present example, the stimulator arrangement is configured to generate electric stimulating signals and configured as described above, namely including the first electrode elements and a common second electrode. Further in this specific not limiting example, the same second electrode is common for the arrays of first electrode elements of both stimulator arrangements 110.

The arrangements of first electrode elements 116 are integral in the nose pads 132 of the glasses. In the present not limiting example, the second electrode 118 is integrated in the temples portion 134 of the glasses. Also, in the present not limiting example, located in the temples portions of the glasses are functional elements of the electronic circuitry (107 in FIG. 1), such as actuator 112 (operable as a pulse generator) and local controller 108 and possibly also a wireless module 135. It should, however, be noted that the electrode 118, as well as at least a battery unit of the electronic circuit 134, may not be located on a template portion of the glasses (i.e., behind the ear when the glasses are in use). For example, all the electrodes 116 and 118 may be located on a portion of the glasses aligned with the front side of the user's face. The inventors have found that such configuration provides for signal collection and identification of blinking effect.

As also exemplified in the figure, the sensing system 122 is properly mounted on the glasses, e.g. on the frame portion.

Figure 4B:
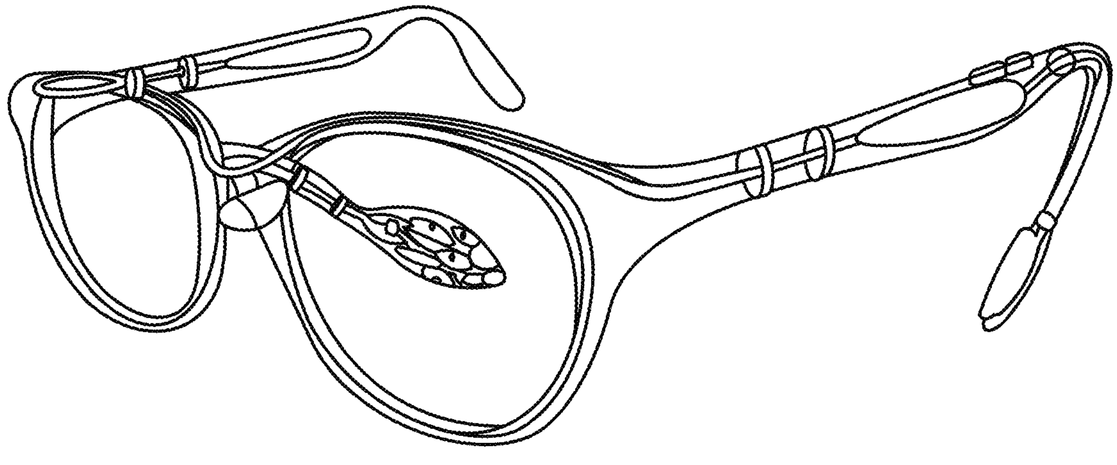

It should be noted that the stimulator 105 may be an autonomous integral unit configured to be mountable on the glasses, e.g. on the nose pads interface 138. FIG. 4B is a picturized illustration of glasses carrying the stimulator 105 of the invention configured as described above.

Figure 4C:
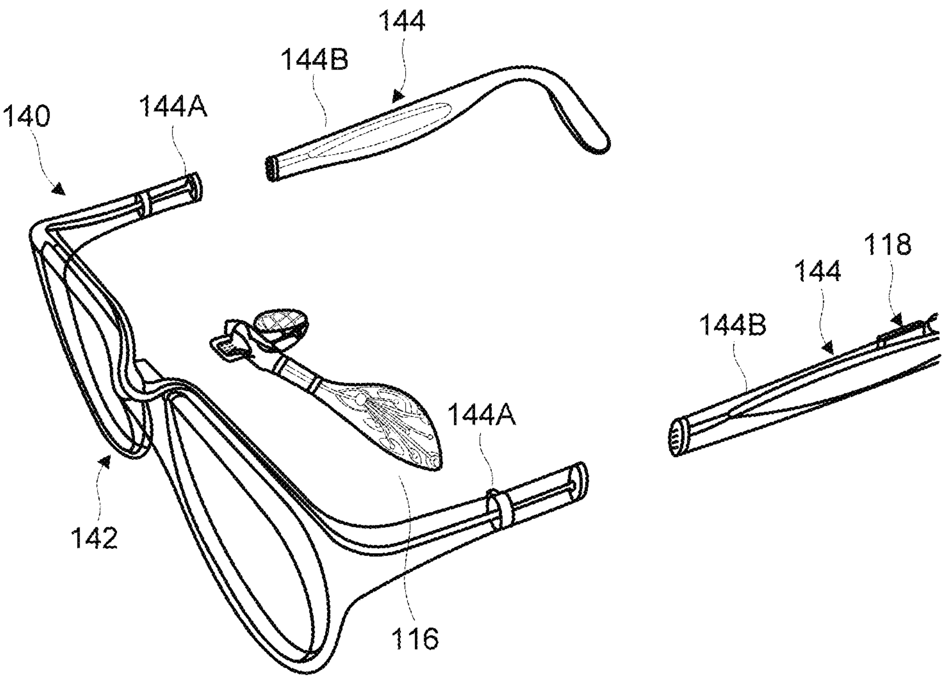
Figure 4D:
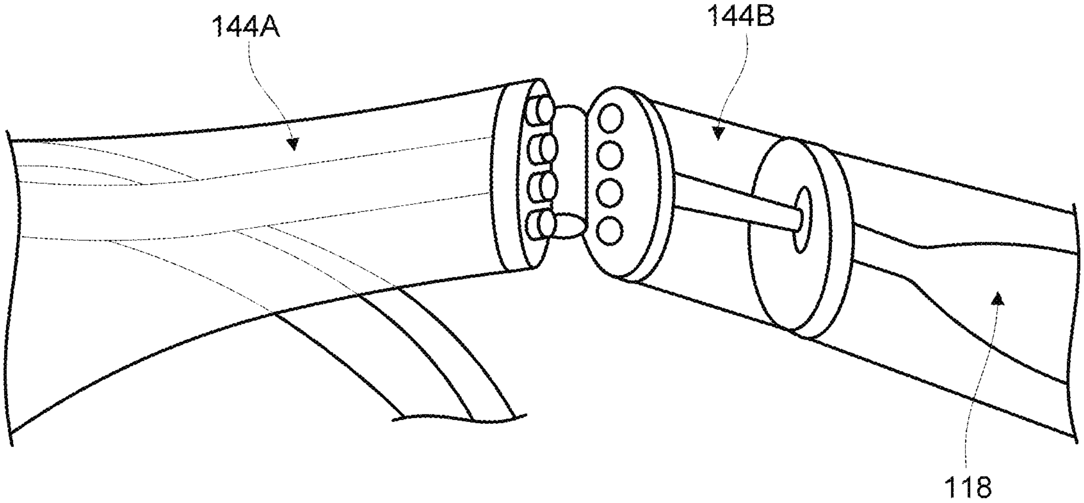

FIG. 4C illustrates a somewhat modified design of glasses 140 enabling simple integration of the stimulator 105 therein. The optical/lens portion 142 of the glasses is of a standard configuration, while each of the temples 144 is configured as a two-part unit, one part 144A being integral with the lens portion 142 and the other part 144B being removably connectable with the part 144A (e.g. via magnetic elements). The part of the stimulator including the first electrode elements 116 is configured for mounting on the nose pads and nose pads interface, while the second electrode and the elements of the electronic circuitry (not specifically shown here) and located in the removable parts 144B of the temples. As shown in FIG. 4D, coupling between the temples' parts 144A and 144B implements the electrical connection between the first and second electrodes and allows operation of the stimulator.

Figure 4E:
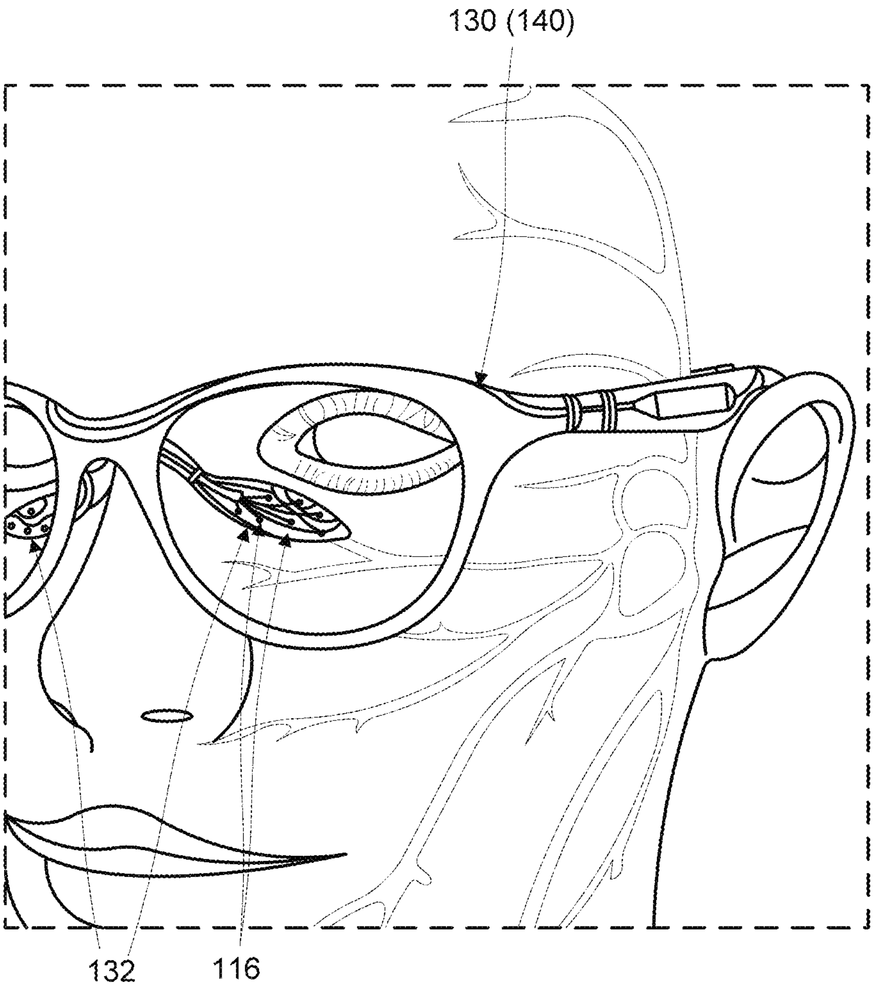

FIG. 4E schematically exemplify the glasses (130 or 140) being worn by the individual and illustrates how one of the interface region of the stimulator defined by the nose pad of the glasses is projected on the nerve circuitry in the respective facial region of interest.

Figure 4F:
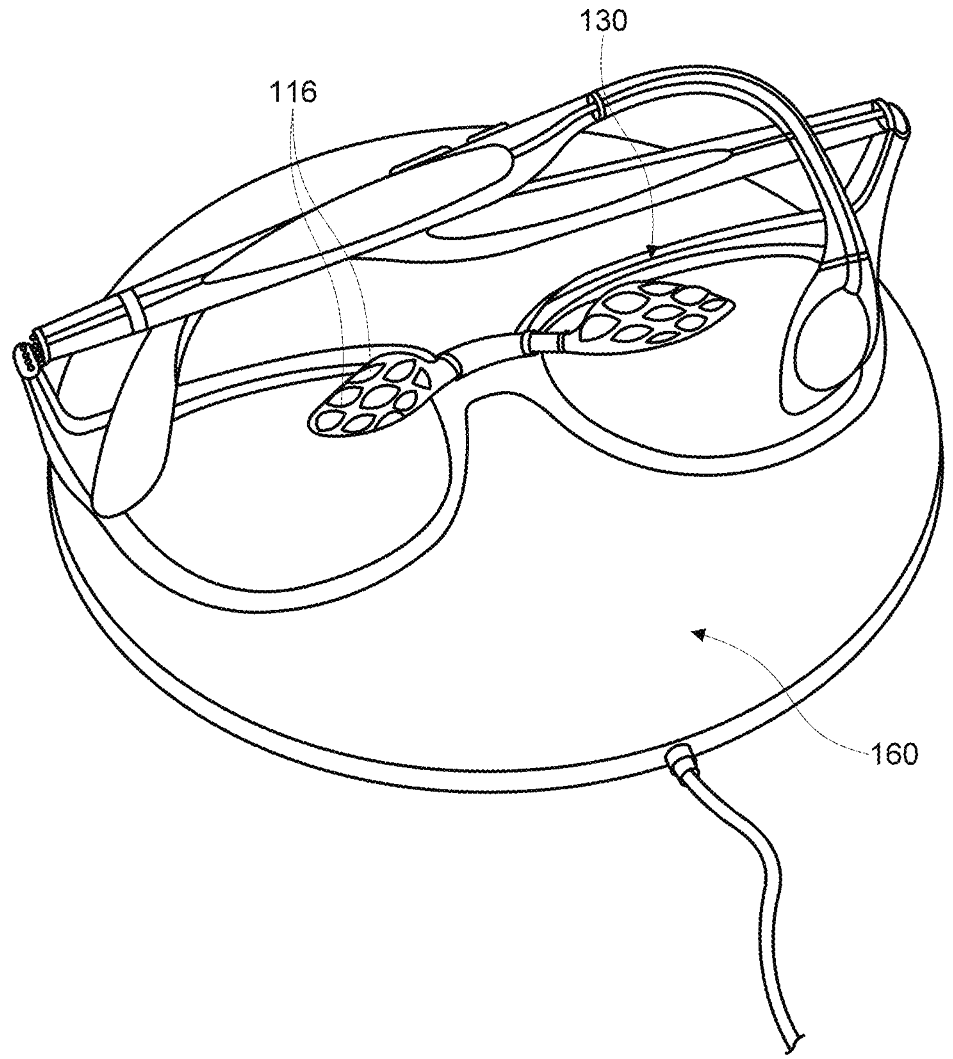

FIG. 4F illustrates glasses 130 carrying the stimulator 105 of the present invention (integral with or mounted on the glasses as described above) placed on a wireless charger 160 thereby enabling charging of the batter of the stimulator.

Accurate positioning of the stimulation elements (first electrodes) over the motor nerve branches is critical for the successful activation of muscle contraction. A number of motor and sensory nerves are dispersed under the skin around the eye but not all generate a blink. Some generate other facial movements while others generate pain sensation. For the stimulation effect to be effective and tolerable generating a blink might not be enough. The blink is to be complete (fully closing the eye), painless and selective-one that generates only a blink and no other facial movements. The way to achieve this goal is by positioning the electrode directly above a nerve generating a blink in a section/location of the nerve that is far enough from another nerve and to use the least stimulation magnitude possible for a complete blink. Even a slight movement of the electrode can disrupt the efficiency of the blink, generate pain or activate other muscles. Hence, identification and activation of the suitable/correctly located stimulating element(s) (electrodes) is important to properly perform the stimulation session.

The array or matrix of the stimulating elements presents a so-called "electrically conductive pixels", each of which may function as an independently controlled stimulating element (electrode). As described above, such array of electrodes, defining an interface region of the stimulator, may be configured to be positioned on skin surface above the motor nerves in the region of interest. As will be described more specifically further below, a calibration process may be employed once to identify user-specific (and possibly eye-specific) sensitivity map data and determine the corresponding characteristic optimal combination of pixel activations for inducing muscle contraction while reducing or minimizing pain and discomfort. Moreover, the technique of the present invention allows flexibility (less accuracy or precision) in positioning the entire interface region (electrodes' matrix or array) over the nerve or nerve circuitry because of the ability of selection of specific electrodes (specific locations) to be addressed in the stimulation session.

The personalized stimulator of the present invention allows to involve in the device operation a selected group/sub-array of the first electrode elements/segments (i.e. a pattern of the first electrode elements independently devised for each eye) to stimulate the blinking function of the eyes. Such personalized selection of the sub-array of individually operated electrode elements is needed because the location map of nerves that are to be electrically activated to cause the periocular muscles' contraction is different within facial structures of different individuals. Moreover, applying electrical signals to other locations within the individual face aligned with/facing the electrode might cause discomfort of the individual and should thus be avoided.

Figure 5:
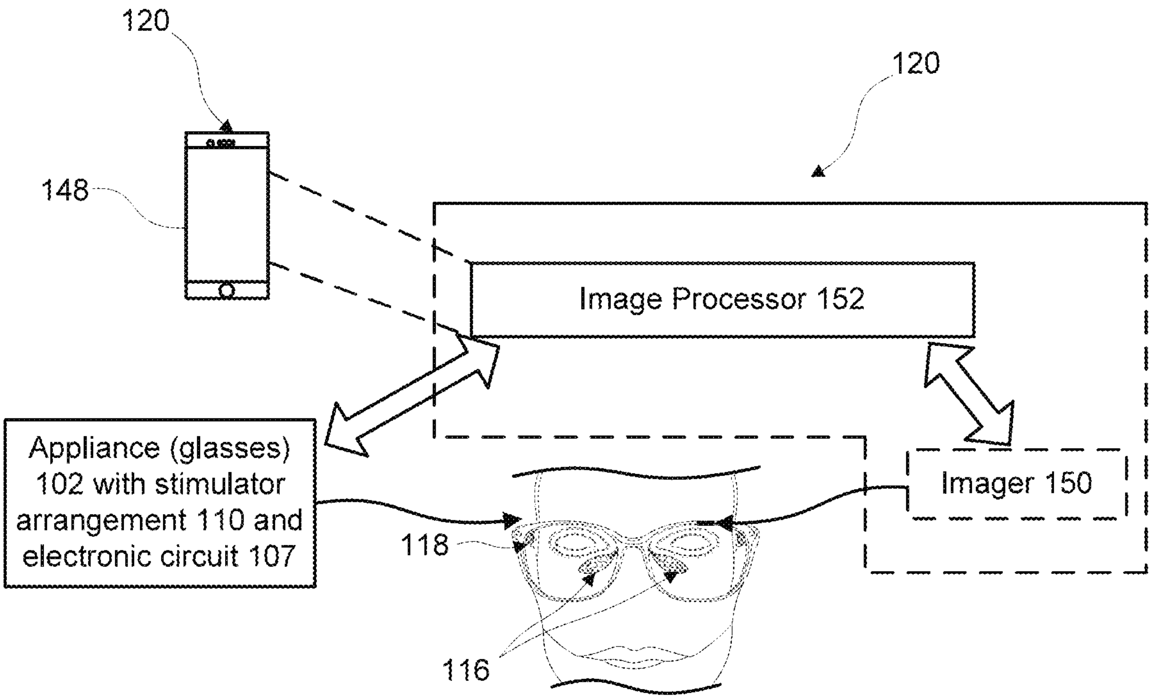
FIG. 5 exemplifies configuration and operation of a calibration system/technique suitable to be used with the present invention.

As described above, calibrating the stimulator to define the sub-array of electrode elements to be used in treatment session for specific individual can be performed once resulting in generation of sensitivity map data (per region of interest for each eye). This can be performed as follows:

Turning now to the above described FIG. 1 as well as to FIG. 5, the appliance 105 with the stimulator (stimulator arrangement 110 and electronic circuit 107) is brought in place, e.g. the glasses with the first electrode elements 116 in the nose pads and the other functional parts in the temples are worn by the individual, and the stimulating elements SE (first electrode elements) are sequentially individually activated/addressed by the controller 108 and the actuator circuit 112 (power supply creating a potential difference between the addressed first electrode and the second electrode) to generate a stimulating electrical signal at the respective location on individual's face. Individual's response data to such stimulating signal is monitored. For each stimulating signal generated by each stimulating element, the response data includes objective data (stimulation related data) about the blinking effect condition (e.g., whether full closure of the eye is achieved), and subjective data about pain/discomfort feeling of the individual caused by this stimulating signal. This subjective data may, generally, be in the form of individual's input about his/her personal feelings (pain/discomfort).

Alternatively or additionally to such individual's input, the subjective data may be collected via imaging technique, i.e. includes analysis of image data collected from the individual's face to learn about individual's reaction to the applied stimulating signals via his/her face motion (mimics). To this end, the calibration stage may utilize the calibration system 120 including at least one imager (camera) 150 and an image processor software 142.

Yet further, alternatively or additionally to the above, sensing signals indicative of the electrical activity (e.g., EMG signals) within the region of interest can be collected and analyzed to create electrical activity maps providing data about electrical activity in the user's face. In the description below such electrical activity signals and electrical activity map are referred to as EMG signals and EMG map. It should, however, be understood that the principles of the present disclosure are not limited to this specific implementation. As described above, the electrical activity can be monitored using EMG and/or EOG and/or EEG techniques. Such sensing signals can be collected from the same electrode with which stimulation is performed, thus eliminating a need for a separate sensor. In other words, the electrode performs both sensing and actuating/stimulating functionalities.

In case the above-described image processing technique is used, the image processor 142 is typically preprogrammed with reference data of the normal face mimics and a degree of change/fluctuation of the face mimics classified as abnormal condition. For each stimulating element being checked during the calibration stage, detection in the response data presence of both of the condition of sufficient stimulating effect (full eye closure during blinking and/or tears production) and normal or allowed/accepted degree of change from normal condition of the face mimics, results in selection of the respective stimulating element for inclusion in the sub-array of such elements. Alternatively, the processor can be preprogrammed to reject the stimulating element from being included in the sub-array of operative elements upon identifying absence in the detected response data of either one or both of the condition of insufficient stimulating effect and abnormal condition of the face mimics, such that the remaining non-rejected stimulating elements form the selected sub-array of the stimulating elements.

Additionally, the calibration procedure may be configured to determine signal strength, and/or pattern/waveform, and/or time pattern for each pixel/electrode element of the matrix.

As described above, the stimulator may be associated with the sensing system (122 in FIG. 1) which includes an imaging system. So, such sensing system may be used in the calibration stage.

As exemplified in FIG. 5, the calibration system 120 may utilize an individual's personal communication device 148, such as his/her phone device, which is properly installed with an image processing software (mobile application) configured as described above. Such software application can be downloaded from a respective server via communication network. Alternatively, the personal communication device may be in data communication with the remote server which is responsive to the image data receive from the phone device to run the image processing and return the result (selection or rejection of the stimulating element) to the electronic circuit 107 of the stimulator, either directly or via the phone device. As also exemplified in FIG. 5, alternatively or additionally, the calibration system 120 may include a camera/imager 150 mounted on the appliance itself (on the frame of glasses) and the image processor 152 may be part of the electronic circuit 107.

The above-described calibration stage results in the individual-specific sensitivity map data SMD which is stored in the memory of the electronic circuit 107 and/or of the smartphone device 148 and is then used to activate the personalized selected sub-array of the stimulating elements to perform each stimulating session.

The individual can then use his personalized stimulator, e.g. a wearable device, which can be operated using a set of interfaces on the device and a mobile application on a computerized end user device such as a smartphone 148.

As described above, the applicator may utilize/be used with the imaging system, e.g. sensing system 122, which may aid in finding the correct position of the device on the individual's face and selection of the operative sub-array (as described above) and assist in repositioning it in future usage. This technique facilitates rapid end user device personal calibration as needed.

It should be noted that, while utilizing the same stimulator, i.e. the same arrangement of stimulating elements, different sub-arrays/groups of the stimulating elements can be optimal for different eye functions, in particular stimulation of blinking effect and tears' production effect.

Figure 6A:
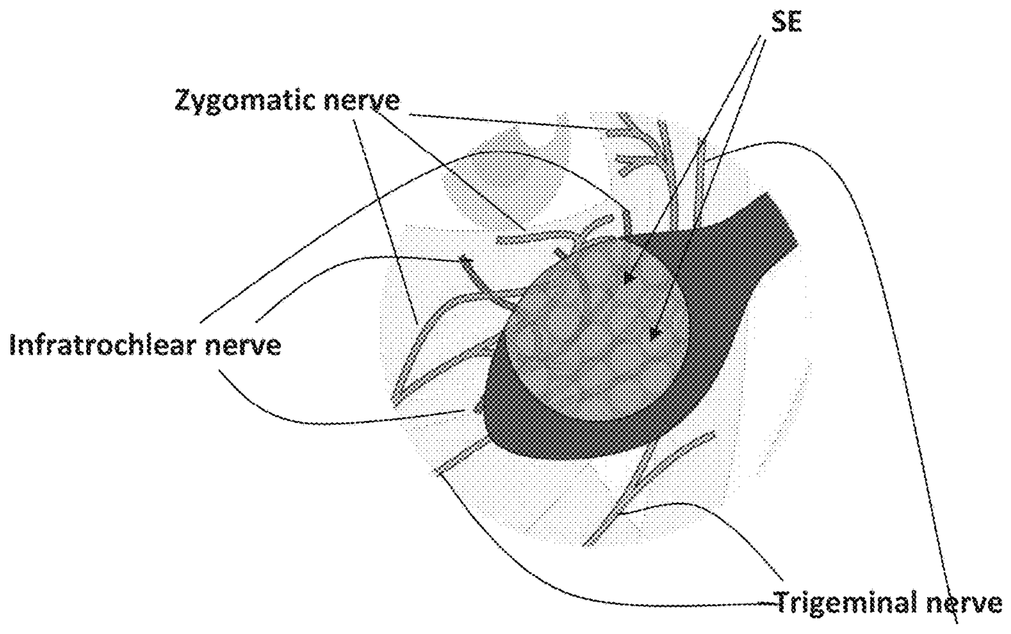
FIGS. 6A to 6C and 7A-7B exemplify different stimulation patterns and their effects selected in accordance with sensitivity map data of the specific individual and the eye function to be stimulated.
Figure 6B:
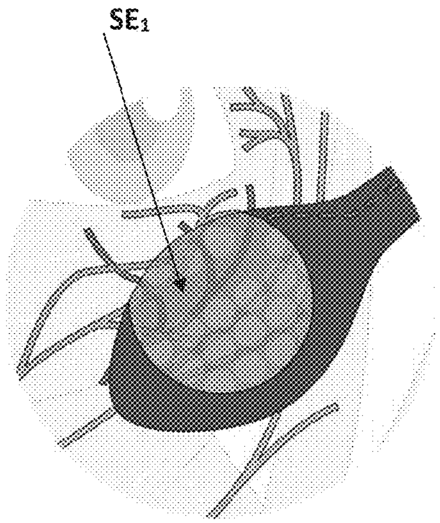
Figure 6C:
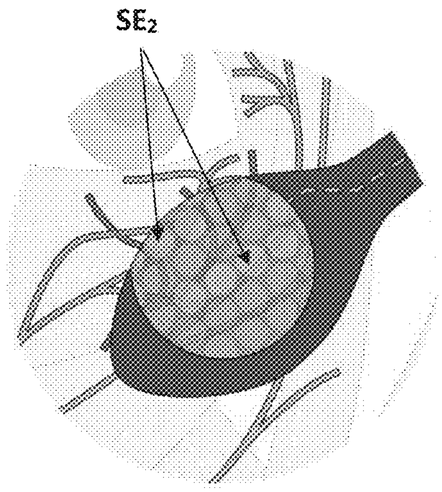

In this connection, reference is made to FIGS. 6A to 6C exemplifying different stimulation patterns SA (selected sub-arrays of stimulating elements) and their effects selected in accordance with sensitivity map data of the specific individual. FIG. 6A exemplifies a stimulator arrangement incorporated in the appliance, e.g. nose pad of glasses. The stimulator arrangement includes the matrix/array of multiple stimulating elements defining/covering all together the interface region IR. This interface region is aligned with/located over the nerve circuitry of the facial region. This nerve circuitry includes zygomatic nerve whose stimulation allows for triggering blinking effect, infratrochlear nerve whose stimulation allows for triggering tears production, and also includes irrelevant branches of the facial nerve including sensory branches of the trigeminal nerve in this area.

FIG. 6B shows the selected sub-array SA1 of the stimulating elements forming a pattern that triggers tearing by stimulating only the infratrochlear nerve, while not causing blinking effect and providing minimal discomfort for the specific individual. FIG. 6C shows the selected sub-array SA2 of the stimulating elements from said arrangement forming a pattern that triggers blinking effect with minimal discomfort for the specific individual by stimulating only the zygomattic nerve.

As can be understood from FIG. 6A, in case the entire interface region is activated using all the stimulating elements in the matrix, blinking would be triggered via zygomatic nerve, tearing would be triggered via the infratrochlear nerve, while at the same time various undesirable effects would be triggered. These include unwanted eyebrows/nose movement through irrelevant branches of the facial nerve, which will cause discomfort by stimulating many sensory branches of the trigeminal nerve in this area.

Figure 7A:
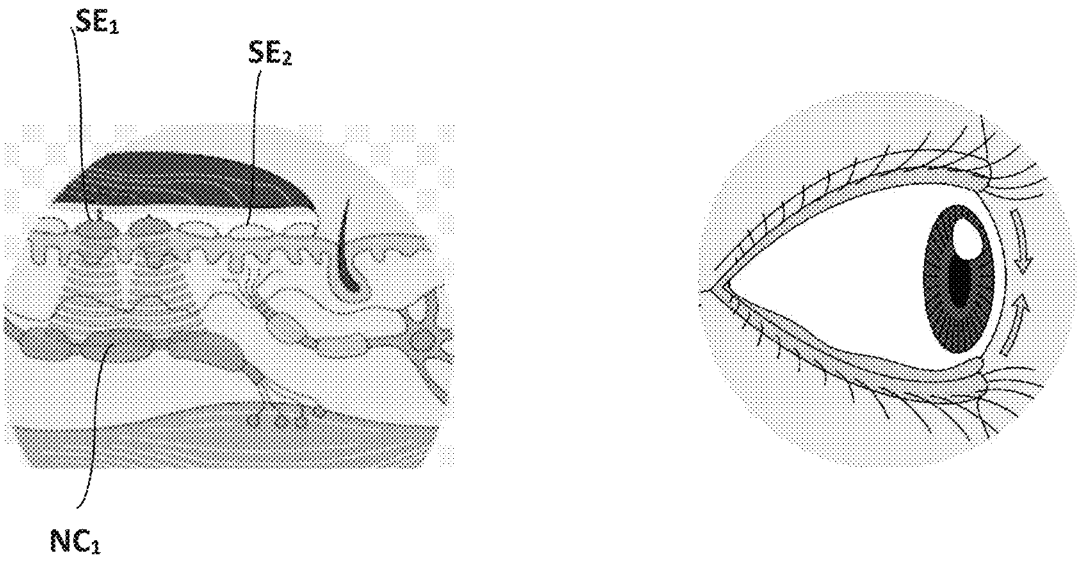
Figure 7B:
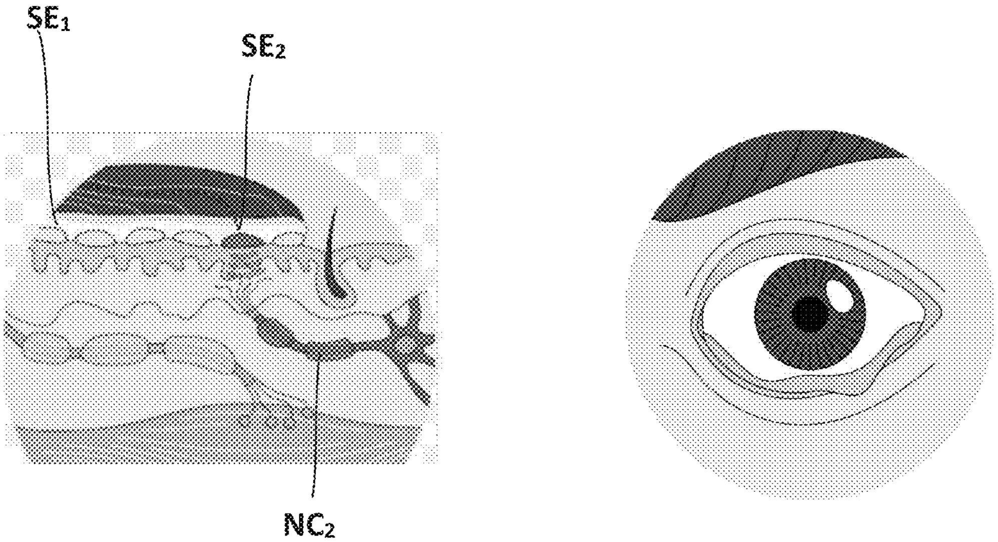

Thus, the same stimulator arrangement (array of stimulating elements) can be used to selectively activate different sub-arrays thereof to generate different stimulating signals stimulating different parts of the nerve circuitry in the region of interest covered by/aligned with the interface region defined by the stimulator arrangement, and accordingly providing different stimulating effects. This is also exemplified in FIGS. 7A and 7B. FIG. 7A illustrates that by actuating the selected sub-array SE1 of the stimulator arrangement and leaving the stimulating elements SE2 inactive, the stimulating signals affect only the nerve(s) NC1 of the nerve circuitry in the region of interest causing blinking effect while eliminating the tears production. FIG. 7B illustrates that by actuating the selected sub-array SE2 of the same stimulator arrangement and leaving the stimulating elements SE2 inactive, the stimulating signals affect only the nerve(s) NC2 of the same nerve circuitry in the region of interest causing the tears production with no blinking effect.

It should be noted that unilateral facial paralysis is the situation where one side of the face is healthy while the other side is paralyzed and unable to blink. The technique of the present invention provides for bilateral blink synchronization, including the inducing of artificial eye closure on both sides, thus significantly reducing the number of spontaneous blinks, and eliminating the necessity of detecting them.

In some examples, monitoring devices may be employed configured to assess of sufficient blinking by analyzing eyelid position during activation. To this end, as described above, the sensing system can be used. This provides the individual with an adaptive tool for personal calibration of the device operation.

In some use examples, no attempt may be made to synchronize facial expressions by blink detection and using source-detector pairs. Instead, both face sides are simultaneously or asynchronously activated, whether the nerve is paralyzed or healthy.

Considering incorporation of the stimulator of the present invention is glasses, the glasses can include various parts that can be quickly and securely assembled and disassembled to enable easy replacement and personalization.

The electrodes can be detached from the frame, and the frame can be detached from the temples. This enables replacement of different parts, for example personalized frames can be selected for different scenarios (personalized frame for face type and style). The temples of the glasses may use conductive hinges that shut off when the glasses are folded to prevent accidental activation when not in use.

In addition, the device may include a condensed electrode matrix in proximity to a specific branch of the facial nerve, e.g., to stimulate a specific movement. It should also be noted that in any of the above-described stimulating devices one or more additional stimulators may be used (i.e., together with the above-described stimulator in the form of matrix/array of individually operable electrode elements/segments). Such additional stimulator(s) may or may not be integral with the same appliance. The additional stimulator may be responsive to the sensing data (typically image data as described above) and may include, for example a physical assembly of any suitable type adapted to notify/bring the individual's attention that blinking is needed, via physical contact (e.g. of a specific pattern) and/or may include software application installed in the individual's personal electronic device (computer, phone, watch) to induce voluntary eye blinking (conscious blinking).

Figure 8:
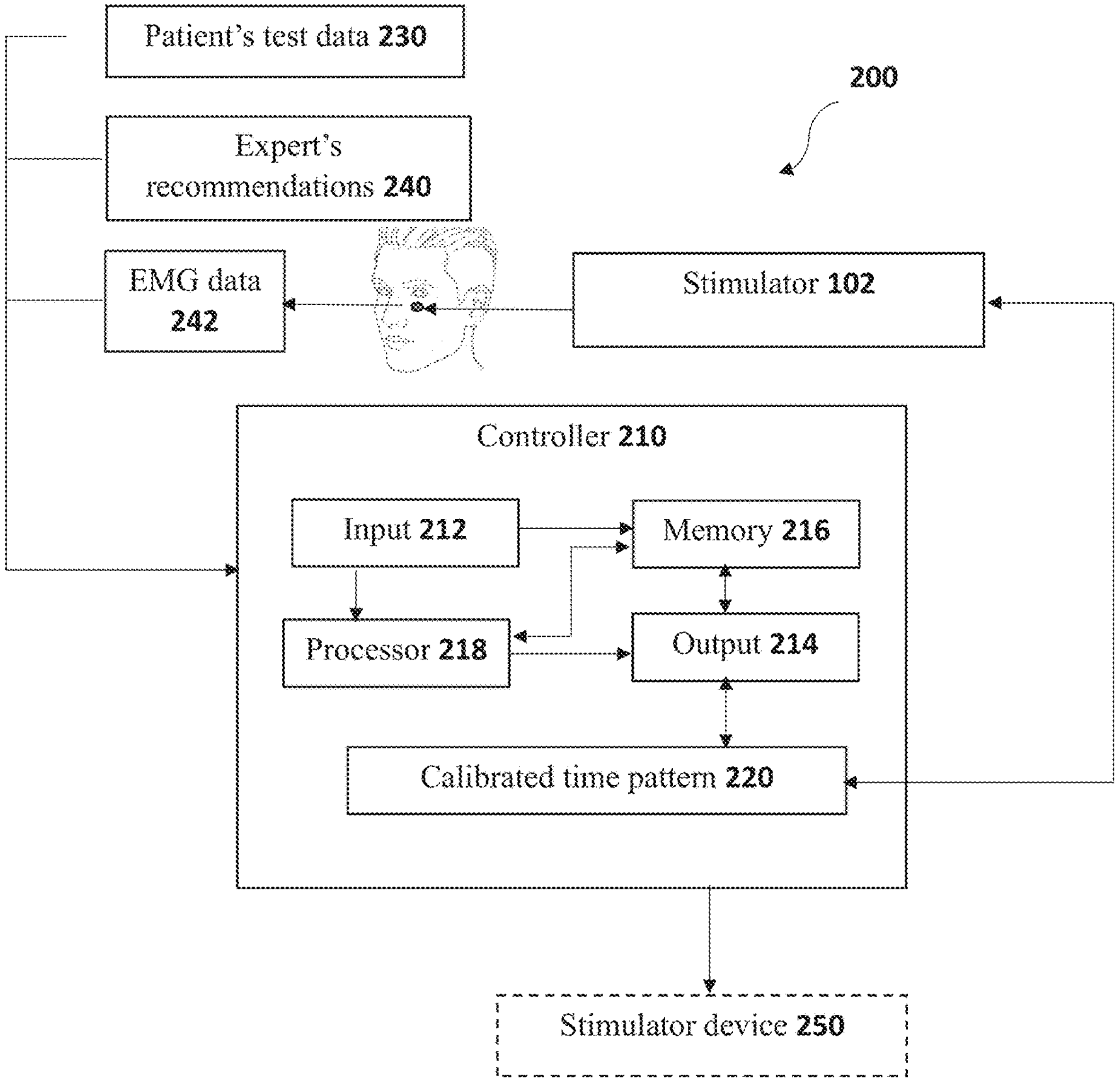
FIG. 8 is a block diagram describing the system of the present disclosure.

Reference is made to FIG. 8 describing, by way of a block diagram, a system 200 of the present disclosure for determining an optimal/calibrated procedure (e.g., time pattern and electrical parameters) for the operation of a stimulator device, generally at 250, to stimulate desired eye activity (ies) prescribed for a specific patient, such as blinking and/or tear production. The system 200 includes a controller 210, which is a computerized device including, inter alia, input utility 212, output utility 214, memory 216, and processor (processing circuitry) 218. The system 200 may be properly connectable to the stimulator device 250.

The stimulator device may be configured as the above-described stimulator 102 of the present disclosure. As described below, the stimulator 102 may be used as the device to be properly calibrated, and also may provide input data to be analyzed, i.e., may be used as a sensing device providing EMG sensing data (sensitivity map).

Input data provided to the controller 210 includes patient's test data 230 which may be indicative of a plurality of test examinations that the patient has undergone. Examples of examinations include Tear Break-up Time that measures the time it takes for the tears to break up after a blink and/or Schirmer test that measures the amount of tears produced over a period of five minutes and/or patient's subjective assessment of the respective eye's state, and/or other tests that will be detailed further below.

Considering the use of the stimulator 102 of the present disclosure, i.e., stimulator including an array/arrangement 110 of individually operable stimulating electrodes each generating a stimulating signal at a respective point/location of the stimulating electrode within an interface region covering a region of interest on the individual's face in a vicinity of the respective individual's eye, the test data 230 (alternatively or additionally to the above tests) includes EMG signals 242 (constituting electrical activity signals) recorded with the same electrode array 110 used for stimulating. Thus, the same electrode array can be used to implement such functionalities as sensing, recording, imaging, mapping to enable to analyze the electrical activity in the user's face. Analysis of such electrical activity allows for crafting personalized stimulation, i.e., determination of stimulation parameters, for specific eye activity (e.g., blinking). This enables to determine blinking schedule or prescription for a specific individual.

Also included in the input data may be expert's recommendations 240 including some initial prescription data serving as patient's specific recommended data for the operation of stimulator device 250 (and/or device 110). It should be noted that in some embodiments of the present disclosure, the expert may be a physician, or may be a computerized utility, which is configured and operable as AI-based (e.g., model-based) analyzer which provides recommendation data based for example on previously performed tests/analyses of stimulation data collected from multiple individuals in relation to specific eye activity.

Thus, the processor 218 analyzes the input data and outputs an optimized calibrated time pattern 220 specifically adjusted to the assessed patient's eye status. It should also be noted that the calibration of the time pattern for a specific stimulator device may be performed prior to or while using the stimulator device.

It should be noted that assessment of the individual's condition may be a combination of such factors/procedures as: analysis by software utilities (processing circuitry); personal preferences and settings the individual chooses through the user interface application; and recommendations provided by a doctor.

The controller 210 records physiological activity, analyzes it, presents the analysis to the individual allowing him/her to respond (e.g., sleeping patterns displayed by a smart watch, which informs the individual of his/her sleeping habits). The controller can communicate this information to a cloud computer where further analysis are performed and the individual's patterns are compared with accepted patterns, and guidance and more analysis are provided. Also, the technique of the present disclosure may enable the individual to share his/her assessment with the doctor, either through online service or through some compiled report that the system generates for the to share with the doctor during an appointment.

Thus, the assessment of the individual's condition can be performed locally on the stimulator device and/or locally on the user/individual's phone and/or remotely on cloud. Considering the use of a smart watch that counts the individual's heartbeat rate (the counting occurs on the watch itself), the presentation of the heartbeat and some of the analysis (comparison of today's heartbeat rate with yesterday or last week's average) is performed on the user's phone or in the cloud, and insights about potential disease or problems are probably performed in the cloud where the data from the user can be compared with data from other users using AI or other recommendation tools set manually by the developers.

It should also be noted that the calibrated time pattern 220 may be adjusted, manually or automatically, to external parameters such as and not limited to temperature, time of day, humidity, pressure, light wavelengths etc.

The resolution of the calibrated time pattern may have sub-second resolutions and the calibration procedure may be applied to both eyes or each eye separately.

In some embodiments, the calibrated time pattern 220 may be used for treatment purposes and in other embodiments, it may be used as prevention.

Figure 9:
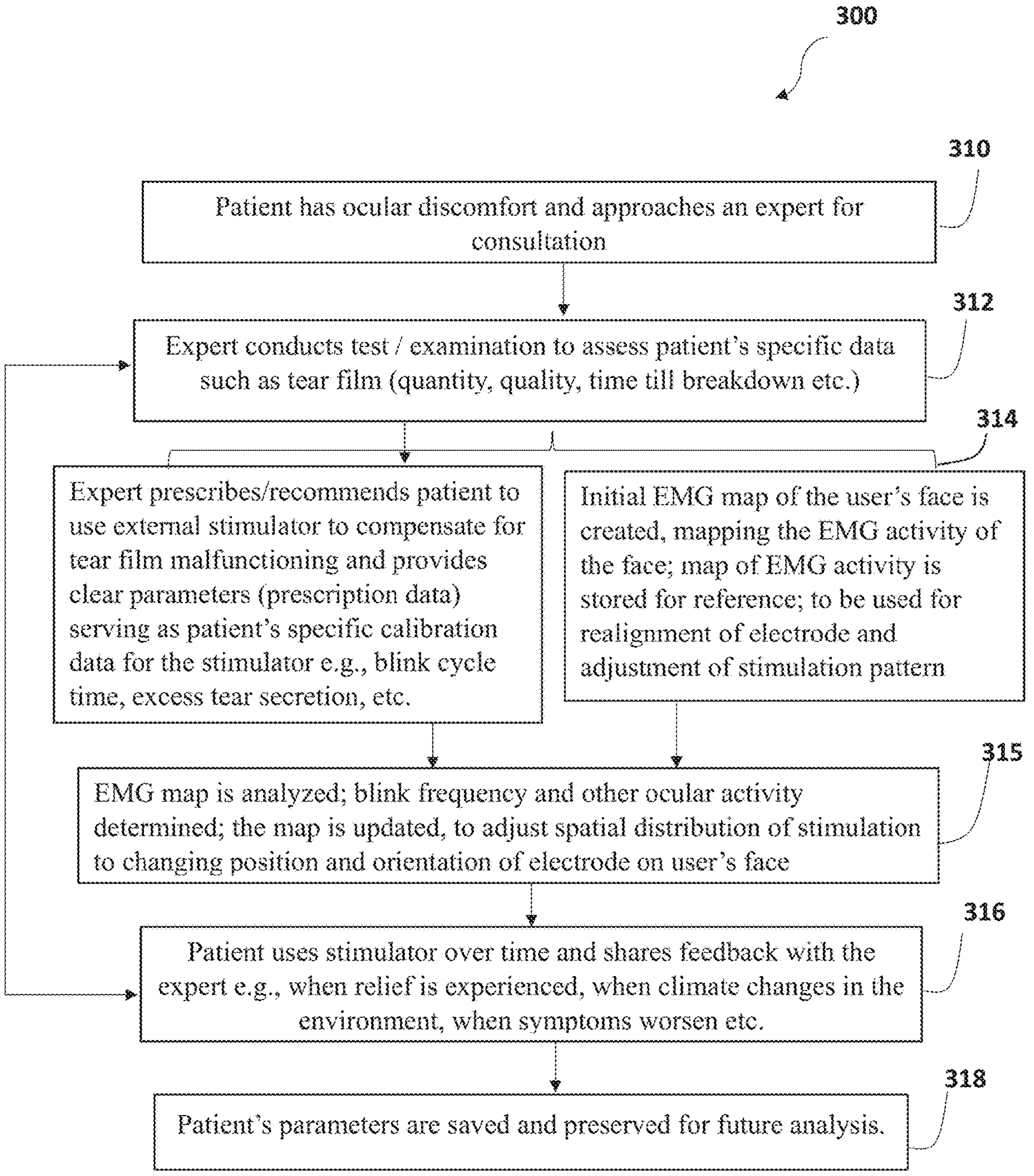
FIG. 9 is a flow diagram describing the method of the present disclosure.

Reference is made to FIG. 9 showing a flow diagram 300 of an exemplary calibration procedure according to the principles of the aspect of the present disclosure.

A patient having an ocular discomfort approaches an expert for consultation (step 310). The patient may interact with an expert (an ophthalmologist, a trained technician, or an autonomous software or device) in their physical presence or through a virtual platform. The expert conducts test(s)/examination(s) (step 312) to assess patient's specific data such as tear film (quantity, quality, time till breakdown etc.).

The expert may then (step 314) prescribe/recommend the patient to use external stimulator to compensate for tear film malfunctioning and provide clear parameters (prescription data) serving as patient's specific calibration data for the stimulator e.g., blink cycle time, excess tear secretion, etc. Specifically, the expert defines the tear film breakup time of the specific patient and mandates, via a designated device (e.g., stimulator device 250 or 110), the time pattern of the blinking reflex prescribed to said patient (constituting patient's specific blinking function) to precede the breakup time with a fresh film formation, i.e., a blink, for said patient. Also, as a part of this step 314, the initial EMG map of the user's face can be created, where the expert (or the user with guidance from software and maybe dedicated hardware) maps the EMG activity of the face and the map is stored for reference throughout the regular usage of the stimulator device. The map is used for realignment of the electrode and adjustment of the stimulation pattern.

It should be noted that in case of use of the stimulator device 110, spatial distribution of the activating electrodes is involved in the calibration procedure. The spatial distribution of the activating electrode is important for a successful stimulation, because the stimulation response is highly affected not only by the electrical parameters of the pulse but also by the spatial properties (i.e. where is the current entering and leaving the body).

In order to calibrate the spatial properties of the stimulation to an individual, the individual may undergo a process similar to when he/she meets an optometrist to determine the lenses number (i.e., some dedicated examination device/s is/are used by the optometrist, and then a prescribed lens number is generated to match the individual's situation). Similarly, for the stimulation, some dedicated mapping/calibration electrode may be used by the individual/expert at the beginning to map the face anatomy, nerves, EMG activity across the face, the response to electrical stimulation across the face, and other spatial physiological properties; and then a personalized stimulation pattern can be tailored for the spatial physiological properties. This "map" or "maps" can later be used by the device to generate highly personalized/optimized stimulations. For example, when the electrode moves, the device detects this movement by comparing the currently recorded EMG signals in the different pixels as compared with the mapped EMG recordings determined in the calibration phase, and then the differences can indicate the movement direction and even the exact new position on the face which can be used to adjust the stimulation pattern accordingly so that the spatial distribution of the pulse over the user's face remains accurate for triggering the desired effect (blinking).

Regarding the blinking effect, the expert may, for example, determine that the patient's tear film breaks on average 5.5 seconds post blinking. In such case, the expert prescribes the patient with the patient's specific blinking function being a calibration function to be used for a stimulation device calibrated to trigger or confirm the presence of a blink every 5 seconds only. The expert may assess additional relevant parameters, such as tears' volume, time-dependent or environment-dependent tear film quality etc. and determine the healthy parameters for various eye activities to be monitored and paced by an eye activity stimulator.

The controller 210 (its processing circuitry 218) continuously analyzes user's EMG data to determine blink frequency, as well as other ocular activity, and updates the map of this electrical activity on the user's face, and the spatial distribution of the stimulation is adjusted to the changing position and orientation of the electrode on the user's face (step 315). This provides insights on the user's health derived from the analysis of the user's EMG activity and its spatial distribution.

The patient uses the stimulator device over time and shares feedback with the expert e.g., when relief is experienced, when climate changes in the environment, when symptoms worsen etc. (step 316). The above-described process may be iterative and thus the initial calibration may change over time. Once an activity interval (optimized eye activity function, e.g., blinking function) is determined and played out, it may change later by revisiting the expert (i.e., performing again from step 312), a self-adjustment by the patient, an informed decision of the eye activity stimulator, and other possible factors. Additionally, the system may share feedback with the expert or user, continuously or at other defined intervals for further analysis.

The patient's parameters are saved and preserved for future analysis (step 318).

The following are some examples of the patient input and/or inspection data to be provided in order to further optimize the calibration procedure. As already mentioned above, the expert questions the patient and performs a series of examinations.

Examples of examinations include, but are not limited to the following:

a) Tear Break-up Time (TBUT): TBUT measures the time it takes for the tears to break up after a blink;
b) Schirmer test: This test measures the amount of tears produced over a period of five minutes;
c) Lissamine Green/Fluorescein staining: These are dyes that are instilled in the eye and can measure the severity of the dry eye by staining the area of the eye that is damaged;
d) Ocular Surface Disease Index (OSDI): This is a subjective questionnaire that measures the impact of dry eye symptoms on a person's quality of life. It consists of 12 questions about symptoms and daily impact on the quality of life;
e) InflammaDry: a new assay that measures the level of matrix metalloproteinase-9 (MMP-9) in the tears. Elevated MMP-9 levels indicate inflammation in the ocular surface, which is associated with dry eye disease;
f) Meibomian Gland Evaluator (MG Evaluation): used to evaluate the health of the Meibomian glands, which are responsible for producing the oily layer of the tear film;
g) Patient subjective assessment;
h) Tear Meniscus Sight;
i) Artificial tears usage frequency;
j) MRB eyelid opening; and
k) Levator examination.

The above inspections/examinations can be implemented using any known suitable respective instruments/tools. Examples of instruments to perform these examinations include, but are not limited to the following:

(i) Tear osmolarity meter: This is an instrument that measures the concentration of the salts in the tears, which can be used to evaluate the severity of dry eye disease;
(ii) Interferometer: This instrument uses infrared light to measure the thickness of the tear film, which can be used to evaluate the stability of the tear film in patients with dry eye disease;
(iii) Non-invasive tear break-up time (NIBUT): This instrument uses a special light to measure the time it takes for the tear film to break up after a blink;
(iv) Infrared meibography: This instrument uses infrared light to take images of the meibomian glands, which can help to evaluate the function of these glands in patients with dry eye disease;
(v) Lipiview: This device is used to evaluate the function of the meibomian glands and the lipid layer of the tear film, which is important for the diagnosis of meibomian gland dysfunction, a common cause of dry eyes; and
(vi) Oculus Keratograph: This device can measure the various layers of the tear film, and its quality, as well as the eyelid's condition and the oil production from the meibomian glands.

As described above, the electrical activity map (e.g., EMG map) can be used for optimizing personalized selection of electrode elements of the stimulator arrangement to be activated as well as electrical parameters of the electrodes, to optimize stimulation results. More specifically, the electric activity map can be used to perform the calibration procedure. The following is an example of such procedure.

Let us consider the stimulator arrangement (110 in FIG. 1), where the electrode elements of such arrangement present contacts, namely individually operable elements that can record different electrical signals and deliver different stimulation signals. These electrode elements/contacts interface with respective locations/sites within the region of interest of individual's face, e.g., skin under the center of the eye, or at the bridge of the nose. Each such site can be presented by coordinates (x,y) in a 2D "unwrapped face map" as will be described below.

When the multi-element electrode of a certain layout (i.e., electrode formed by a certain arrangement or array/matrix of the electrode elements/contacts) is positioned on the face with certain position data/orientation (x,y, θ), this position data determines mapping (relative position/alignment) between the contacts and the facial sites.

The technique of the present disclosure utilizes creation of features maps, where the term "features" refers to data indicative of electrical activity signals. These may be the electrical signals themselves or any suitable representation/function of the electrical signals being collected. The creation of such features maps can be performed as follows: The sensing data indicative of electrical activity signals, termed here EAS, is collected and processed for each individual contact presenting a feature, and this data is joined with spatial information about where the sensing data originated from (i.e., location/position data of the respective site). These two types of information, processed sensing data (feature) and the location data, are combined into the features map.

Figure 10A:
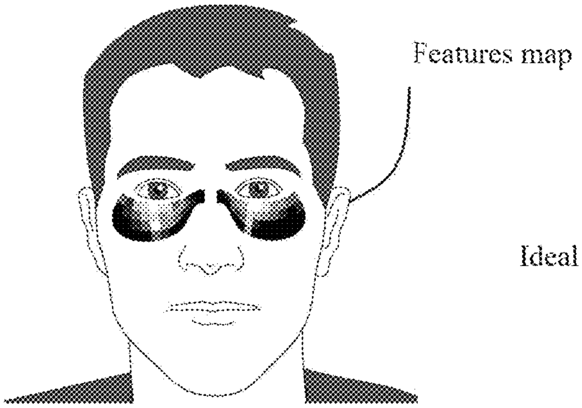
FIGS. 10A and 10B exemplify the technique of the present disclosure to adjust the stimulator for highly personalized operation to apply optimal stimulation signals to optimal locations on the patient's face to achieve the desired eye activity, where the technique utilizes features map (FIG. 10A) to identify ideal stimulation locations (FIG. 10B).

Such recorded features map is exemplified in FIG. 10A, where the contacts (electrode elements) at their respective locations marked by colors from black to white correspond to features values from the small to high values.

The processing of the sensing data to form the respective feature can be implemented using any suitable technique. For example, this can be implemented as follows:

Raw EAS data is recorded from each of the individual contacts of the electrode. This raw data undergoes filtering and cleaning of the recorded signals (e.g., using bandpass filters for the EAS spectrum), and the so-filtered signals are enveloped, e.g., to form Root-Mean-Square (RMS) envelope.

Such signal processing techniques are known per se and therefore need not be described in detail, except to note the following: For EMG signal, the RMS envelope is typically determined/calculated using a moving window approach, and the RMS calculation provides the most insight on the amplitude of the EMG signal since it gives a measure of the power of the signal, while producing a waveform that is easily analyzable.

Then, time windows (sample windows) where events of interest occur (i.e. blinking) are detected. Some further calculation/processing may be applied to the sample windows. The suitable calculation may be that yielding a scalar/vector/tensor per each contact. For example, the scalar data may include: area under the curve (AUC) of the samples window for the most recent blink being detected, peak-to-peak amplitude of that window, the index of the sample in that window (temporal index) where the AUC accumulated to 20% of the total AUC of the full window, etc. The vector data may include: any of the above-mentioned scalar features calculated per each of the last N detected blinks, the original raw data samples, the Fourier transformation/spectral analysis of the frequencies in the EAS signal per each contact, etc. The tensor data (N-dimensional vector) may include: any of the above-mentioned vector features calculated per the last K detected blinks, list of multiple of the above-mentioned vector features calculated per the last K blinks, data provided by some neural network that was fed with the raw sensor data (or some processing of such data as the case may be).

These scalars/vectors/tensors data collectively referred to herein as features, joined with their associated/related spatial data (location data) can be used for realignment process, as described further below.

For the purposes of the present disclosure, the features of interest are features that describe/present the following properties (required for convergence of gradient-based optimization techniques): "Consistency"/"Consistency across blinks" meaning that the same sites are characterized by similar features when calculated on signals from different blinks; and "Variability"/"Variation between sites" meaning that different sites (specifically, sites that are spatially distal) are characterized by different features of signals from the same blink.

Identifying the features with the above properties is needed because the realignment process/algorithm used in the technique of the present disclosure is aimed at guessing the orientation of the electrode (multi-element electrode) based on the recorded EAS data from the electrode contacts, by comparing the features from recent blinks recorded by the electrode with a previously calibrated features map where the features are associated with spatial information (coordinates on a 2D unwrapped face map).

The following is a specific, not limiting, example of the optimization technique of the present disclosure to craft a highly personalized selection of contacts and electrical parameters, so that a stimulation results in a pure, painless blink. The optimization technique includes calibration, realignment, and stimulation adjustment stages.

The calibration stage is performed once, or once in a while, per patient with the expert's assistance. This stage may include the following steps:

- Face Flattening/Unwrapping step. This includes creation of a 2D unwrapped image of the face with the electrode (multi-element electrode or electrode arrangement), where the face is mapped to a standard 2D coordinate system, also known in computer graphics as a texture map, or a UV map. For example, the known "canonical face" map can be used (which is typically used for facial recognition);
- Annotation step, including extracting the site locations of each electrode contact from said unwrapped image of the face;
- Features extraction step, including analysis of the recorded EAS signals at each contact/site;
- Interpolation step, including creating, from the features and their locations data, an interpolated map that can be sampled continuously at any site. The interpolation strategy can be any of the following: linear, Delaunay-linear, cubic, etc.

The realignment stage is performed occasionally on a daily basis and even multiple times during the same use, automatically by the system with no need of an expert. The realignment stage may include the following steps:

- Features Extraction step, including recording new signals from the operational electrode;
- Search step, including hypothesizing/predicting, based on the extracted features and the known layout of the electrode, the most reasonable orientation on the calibrated features map that would explain the observed features. This search algorithm uses an error function that compares the extracted features at the electrode contacts, with the calibration features map at the hypothesized/predicted electrode orientation. Converging to an optimal orientation can be achieved with various optimization techniques, including but not limited to: Hill Climbing/Gradient Descent, Stochastic Gradient Descent, Random-Restart Hill Climbing/Gradient Descent, etc.

Upon identifying the orientation of the electrode, the stimulation adjustment stage is performed utilizing a map of stimulation effects. Such map can be obtained by trial and error, or by correlations to the EAS features map. The stimulation effects map provides data about the stimulation effect of each site on the face. This map is analyzed using the found orientation of the electrode, and provides data indicative of which contacts of the electrode are above the sites that are to be stimulated. This information is used to provide highly personalized selection of contacts and electrical parameters required for effective stimulation of painless blinking.

Figure 10B:
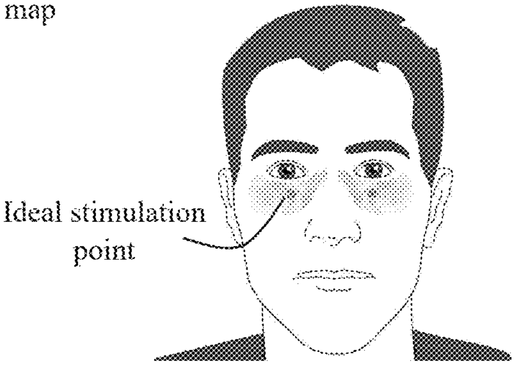

FIG. 10B exemplifies an ideal stimulation point for optimal blink results with minimal pain/discomfort. The above-described algorithm utilizes the EAS features map to locate such point(s).

It should be noted that any digital computer system, unit, device, module and/or engine exemplified herein can be configured or otherwise programmed to implement the technique of the invention as described above. The software products/applications needed to implement the invention, as described above, may be implemented as a computer program product that may be tangibly embodied in an information carrier including, for example, in a non-transitory tangible computer-readable and/or non-transitory tangible machine-readable storage device. The computer program product may be directly loadable into an internal memory of a digital computer, comprising software code portions for performing the processes as disclosed above.

The processes described above may be implemented as a computer program that may be intangibly embodied by a computer readable signal medium. A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a non-transitory computer or machine-readable storage device and that can communicate, propagate, or transport a program for use by or in connection with apparatuses, systems, platforms, methods, operations and/or processes discussed herein.

The terms "non-transitory computer-readable storage device" and "non-transitory machine-readable storage device" encompasses distribution media, intermediate storage media, execution memory of a computer, and any other medium or device capable of storing for later reading by a computer program implementing embodiments of the technique described above. A computer program product can be deployed to be executed on one computer or on multiple computers at one site or distributed across multiple sites and interconnected by one or more communication networks.

The term "engine" may comprise one or more computer modules, wherein a module may be a self-contained hardware and/or software component that interfaces with a larger system. A module may comprise a machine or machines executable instructions. A module may be embodied by a circuit, or a controller programmed to cause the system to implement the method, process and/or operation as disclosed herein. For example, a module may be implemented as a hardware circuit comprising, e.g., custom VLSI circuits or gate arrays, an application-specific integrated circuit (ASIC), off-the-shelf semiconductors such as logic chips, transistors, and/or other discrete components. A module may also be implemented in programmable hardware devices such as field programmable gate arrays, programmable array logic, programmable logic devices and/or the like.

It is appreciated that certain features of the invention, which are, for clarity, described in the context of separate embodiments or example, may also be provided in combination in a single embodiment. Conversely, various features of the invention, which are, for brevity, described in the context of a single embodiment, example and/or option, may also be provided separately or in any suitable sub-combination or as suitable in any other described embodiment, example or option of the invention. Certain features described in the context of various embodiments, exam pies and/or optional implementation are not to be considered essential features of those embodiments, unless the embodiment, example and/or optional implementation is inoperative without those elements.

The invention claimed is:

1. A device for stimulating one or more eye functions of individual's eye, said device comprising a stimulator which is configured to be incorporated in or mountable on an appliance attachable to individual's face and comprises a respective at least one stimulator arrangement, the stimulator arrangement defining an interface region for covering a region of interest on the individual's face in a vicinity of the respective individual's eye, the stimulator comprising a local controller for operating said at least one stimulator arrangement to apply a stimulating effect on one or more nerves in the region of interest to thereby affect at least one predetermined eye function; wherein (i) the stimulator arrangement comprises an array of stimulating elements, each stimulating element being individually operable by said local controller to generate a stimulating signal at a respective location of said stimulating element within said interface region; and (ii) said local controller is configured and operable to activate a predetermined individual-specific sub-array of the stimulating elements from said array of the of stimulating elements during a stimulation session, wherein locations of the stimulating elements of the sub-array being activated within the interface region provide a desired spatial pattern of the stimulating effect to be applied while avoiding applications of the stimulating effect outside said locations within the interface region.

2. The device according to claim 1, wherein the local controller is configured and operable to utilize predetermined data indicative of an individual-specific facial nerve's sensitivity map of the individual, predetermined at a calibration stage performed once for said individual, to define the selected sub-array of the stimulating elements for use in stimulation sessions.

3. The device according to claim 1, wherein said stimulator arrangement is configured and operable to generate electric stimulating signals.

4. The device according to claim 3, wherein said stimulator arrangement comprises an electrodes arrangement configured and operable to generate the stimulating effect associated with neuro-muscular electrostimulation (NMES) of said one or more nerves.

5. The device according to claim 4, wherein said electrodes arrangement is configured and operable to generate sensing signals indicative of an electrical activity map of the individual's face within the interface region.

6. The device according to claim 4, wherein:

(i) said stimulator arrangement comprises first and second electrodes, wherein the first electrode is configured to be attached to and extend along said interface region and is formed by said array of first electrode elements, each being individually operable by the controller to form an electrode pair with the second electrode to apply NMES signal to a respective location of the first electrode element within said interface region; and (ii) said local controller is configured and operable to activate a selected sub-array of said array of the first electrode elements whose locations define a desired spatial pattern of NMES signals to be applied while avoiding applications of NMES signals outside said locations within the interface region, resulting in safety and optimal nerves' stimulation and muscle contraction.

7. The device according to claim 1, wherein the local controller is configured and operable to carry out at least one of the following:

utilize operational data indicative of a predetermined time pattern of activation of the selected sub-array of the stimulating elements; and communicate with a sensing system providing sensing data indicative of the individual eyes' condition.

8. The device according to claim 1, wherein the local controller is configured and operable to communicate with a sensing system providing sensing data indicative of an individual's condition, the device being characterized by at least one of the following:

the sensing system is integral with the appliance carrying the stimulator;

the local controller is configured and operable to communicate with the sensing system and is responsive to sensing data originated in the sensing system, to selectively activate said selected sub-array of the electrode elements;

the sensing system is an imaging system providing the sensing data indicative of the individual eye's condition;

the sensing system is integral with the stimulator arrangement providing the sensing data indicative of an electrical activity map of the individual's face within the interface region.

9. The device according to claim 8, wherein the local controller is configured and operable to affect stimulation of the eye activity via the selected sub-array of the stimulating elements upon identifying, from the sensing data, the individual eye's condition corresponding to absence of said eye activity during a predetermined time interval.

10. The device according to claim 1, characterized by one of the following:

said appliance comprises glasses wearable by individual; and said appliance is a label.

11. The device according to claim 1, wherein said appliance comprises glasses wearable by individual, said glasses being one of the following types: vision correcting glasses, sunglasses, vision correcting sunglasses, virtual/augmented-reality glasses.

12. The device according to claim 6, wherein said appliance comprises glasses wearable by individual, the first electrode being integral with a nose pad of the glasses, and the second electrode being located in temples of the glasses.

13. The device according to claim 12, wherein said glasses are one of the following types: vision correcting glasses, sunglasses, vision correcting sunglasses, virtual/augmented-reality glasses.

14. The device according to claim 1, said appliance comprises glasses wearable by the individual, the device being configured to be mounted on the glasses.

15. Glasses wearable by an individual, said glasses comprising the device of claim 1 and being configured as one of the following types: vision correcting glasses, sunglasses, vision correcting sunglasses, virtual/augmented-reality glasses.

16. The glasses according to claim 15, wherein the stimulator arrangement is integrated withing nose pads of the glasses.

17. The glasses according to claim 16, wherein the stimulating elements of the stimulator arrangement comprise an array of first electrode elements, each being individually operable by the controller to form an electrode pair with a second electrode to apply the stimulating electrical signal to a respective location of the first electrode element within said interface region; the second electrode being located within temples of the glasses.

18. An eye function stimulation system comprising the device according to claim 1, and at least one additional stimulator of a different type.

19. The system according to claim 18, characterized by at least one of the following:

said at least one additional stimulator is integral with said appliance;

said at least one additional stimulator is configured and operable to be responsive to sensing data indicative of individual eyes' condition and generate a stimulation effect to notify the individual that said eye function is to be initiated to thereby induce voluntary conscious eye function; and said at least one additional stimulator comprises a computerized utility installed in individual's personal electronic device and configured and operable to generate, in response to the sensing data, the stimulation effect embedded in displayed data exposed to individual's eyes to thereby induce voluntary conscious eye function.

20. The system according to claim 18, wherein said at least one additional stimulator is configured and operable to be responsive to sensing data indicative of individual eyes' condition and generate a stimulation effect to notify the individual that said eye function is to be initiated to thereby induce voluntary conscious eye function, said at least one additional stimulator including a physical assembly adapted to generate the stimulation effect via a physical contact with individual's body.

21. The system according to claim 20, wherein said physical contact has a predetermined contact application pattern.

22. The system according to claim 18, wherein said at least one additional stimulator comprises a computerized utility installed in individual's personal electronic device and configured and operable to generate, in response to the sensing data, the stimulation effect embedded in displayed data exposed to individual's eyes to thereby induce voluntary conscious eye function, the sensing system being carried by the individual's personal electronic device to which user's eyes are exposed.

* * * * *